(12) United States Patent
Mekada et al.

(10) Patent No.: US 7,659,441 B2
(45) Date of Patent: Feb. 9, 2010

(54) CD9/CD81 DOUBLE-DEFICIENT NON-HUMAN ANIMAL

(75) Inventors: Eisuke Mekada, Osaka (JP); Kenji Miyado, Tokyo (JP); Isao Tachibana, Osaka (JP); Yoshito Takeda, Osaka (JP)

(73) Assignee: Osaka Industrial Promotion Organization, Osaka-Shi (JP)

( * ) Notice: Subject to any disclaimer, the term of this patent is extended or adjusted under 35 U.S.C. 154(b) by 190 days.

(21) Appl. No.: 11/293,388

(22) Filed: Dec. 5, 2005

(65) Prior Publication Data

US 2006/0288435 A1 Dec. 21, 2006

Related U.S. Application Data

(63) Continuation of application No. PCT/JP2004/008261, filed on Jun. 7, 2004.

(30) Foreign Application Priority Data

Jun. 6, 2003 (JP) .............................. 2003-162916

(51) Int. Cl.
*A01K 67/027* (2006.01)
*A01K 67/00* (2006.01)
*G01N 33/15* (2006.01)

(52) U.S. Cl. ................................ 800/18; 800/3; 800/21
(58) Field of Classification Search .................... 800/18, 800/3, 21
See application file for complete search history.

(56) References Cited

OTHER PUBLICATIONS

Wigley et al. (1994) Reprod. Fertil. Dev., vol. 6, 585-588.*
Mullins et al. (1996) J. Clin. Invest., vol. 98(11), S37-S40.*
Wall (1996) Theriogenology, vol. 45, 57-68.*
T. Funakoshi, et al.; "Expression of tetraspanins in human lung cancer cells; frequent downregulation of CD9 and its contribution to cell motility in small cell lung cancer;" *Oncogene*; vol. 22; No. 5; Feb. 6, 2003; pp. 674-687.
Y. Tanio, et al.; "CD9 molecule expressed on stromal cells is involved in osteoclastogenesis;" *Experimental hematology*; vol. 27; No. 5; May 1999; pp. 853-859.
S. Hayashi, et al.; "The CD9 molecule on stromal cells;" *Leukemia & lymphoma*; vol. 38; Nos. 3 to 4; Jun. 2000; pp. 265-270.
Y. Takeda, et al.; "Tetraspanins CD9 and CD81 function to prevent the fusion of mononuclear phagocytes;" *Journal of Cell Biology*; vol. 161; No. 5; Jun. 9, 2003; pp. 945-956.

Maecker, H. T., et al.; "Normal Lymphocyte Development but Delayed Humoral Immune Response in CD81-null Mice;" *J. Exp. Med.*; vol. 185, No. 8, pp. 1505-1510. (Apr. 1997).
Miyado K., et al.; "Requirement of CD9 on the Egg Plasma Membrane for Fertilization;" *Science*; vol. 287, pp. 321-324. (Jan. 2000).
Biskobing, D. M.;"COPD and Osteoporosis;" *Chest*; vol. 121, No. 2, pp. 609-620 and cover page. (Feb. 2002).
Wert, S. E., et al.; "Increased metalloproteinase activity, oxidant production, and emphysema in surfactant protein D gene-inactivated mice;" PNAS; vol. 97, No. 11, pp. 5972-5977. (May 2000).
Morris D. G., et al.; "Loss of integrin αvβ6-mediated TGF-β activation causes Mmp12-dependent emphysema;" *Nature*; vol. 422, p. 169-173. (Mar. 2003).
T. Miyazaki, et al.; "Normal development but differentially altered proliferative responses of lymphocytes in mice lacking CD81;" *The EMBO Journal*; vol. 16, No. 14, pp. 4217-4225. (1997).
Sharon A. McGrath et al.; "Oocyte-Specific Expression of Growth/Differentiation Factor-9"; Molecular Endocrinology; 1995; vol. 9; No. 1; pp. 131-136.
Jennifer L. Dube et al.; "The Bone Morphogenetic Protein 15 Gene Is X-Linked and Expressed in Oocytes"; Molecular Endocrinology; 1998; vol. 12, No. 12; pp. 1809-1817.
Daulat R.P. Tulsiani et al.; "Mammalian Fertilization: A Carbohydrate-Mediated Event"; Biology of Reproduction 57; 1997; pp. 487-494.
Kaji et al.; "The gamete fusion process is defective in eggs of Cd9-deficient mice"; *Nature Genetics*; vol. 24; Mar. 2000; pp. 279-282.
Tsitsikov et al.; "Impaired CD 19 expression and signaling, enhanced antibody response to type II T independent antigen and reduction of B-1 cells in CD81-deficient mice"; *Proc. Natl. Acad. Sci.* USA; vol. 94; pp. 10844-10849; Sep. 1997; Immunology.
Le Naour et al.; "Severely Reduced Female Fertility in CD9-Deficient Mice"; *Science* 287, 319(2000); DOI: 10.1126/science.287. 5451.319; pp. 319-321.

* cited by examiner

*Primary Examiner*—Anne Marie S Wehbe
(74) *Attorney, Agent, or Firm*—Kratz, Quintos & Hanson, LLP

(57) ABSTRACT

An object of the invention is to provide a non-human animal which can be utilized as a model animal well exhibiting a pathological condition of low-turnover type of osteoporosis and chronic obstructive pulmonary disease, for screening therapeutic agents for osteoporosis or therapeutic agents for chronic obstructive pulmonary disease, etc. The invention includes a non-human animal, wherein a gene coding for CD9 and a gene coding for CD81 are deficient at least in somatic cells; and a method to use the non-human animal as an osteoporosis model animal, including a step of measuring the degree of inhibition in the osteogenesis, and a method to use the non-human animal as a chronic obstructive pulmonary disease model animal, including a step of measuring the degree of a phenotype similar to chronic obstructive pulmonary disease.

9 Claims, 19 Drawing Sheets

(3 of 19 Drawing Sheet(s) Filed in Color)

Fig. 1

Mouse CD9 entire DNA sequence

```
   1 cccttctgtc ccagtcgttc gtgcctcttg tcccacgcaa ctccagcttg taccatgccg
  61 gtcaaaggag gtagcaagtg catcaaatac ctgctcttcg gatttaactt catcttctgg
 121 ctcgctggca ttgcagtgct tgctattgga ctatggctcc gattcgactc tcagaccaag
 181 agcatcttcg agcaagagaa taaccattcc agtttctaca caggagtgta cattctgatt
 241 ggagccgggg ccctcatgat gctggttggt ttcctgggct gctgtggagc tgtacaagag
 301 tcccagtgca tgctgggatt gttcttcggg ttcctcttgg tgatattcgc cattgagata
 361 gccgccgccg tctggggcta tacccacaag gatgaggtga ttaaagaact ccaggagttt
 421 tacaaggaca cctaccaaaa gttacggagc aaggatgaac cccagcggga aacactcaaa
 481 gccatccata tggcgttgga ctgctgtggc atagctggtc ctttggagca gtttatctcg
 541 gacacctgcc ccaagaaaca gcttttggaa agtttccagg ttaagccctg ccctgaagcc
 601 atcagtgagg tcttcaacaa caagttccac atcattggag cagtgggtat cggcatcgcc
 661 gtggtgatga tcttcggcat gatcttcagc atgatcctgt gctgcgccat ccgcaggagc
 721 cgagaaatgg tctagagtct gcccaacccc gagcaggaac aacggccctg aagactgtcc
 781 gggccatttg ggttttttttt gccactaata ttagtattca ttatgcattt ctaaataaca
 841 gtcattctgt ttgtcctttt aatgctttat tcattattga catttgtagt tgagggatcc
 901 gggggttcaa tttatttga tttttttttt tggttgttta ttttgcttg ttatgttaag
 961 caaaatcct gcaatgaaag gtactatatt tgccagactc tagacataag atattgtaca
1021 taaagagaat ttttttgcc tttaaataga taaaagtatc tatcagataa aaatcaggtt
1081 gtaagttata ttgaagacaa tttgatacat aataaaagat tataacagtg
```

Fig.2

Mouse CD81 entire DNA sequence

```
   1 gcgagcgcgt ccttgcttca aagagatagt gactctcgcg cctccggcta ggcctccagc
  61 ccttctctac cctacgtctc attctccgca acgcagttct ccggcccgca agcgctccag
 121 gctatctgcc agtcccggac cccggtactg cgtccccata ccgcccgctc caggaccaat
 181 ccaagctccg caggccgcgc accgccatgg gggtggaggg ctgcaccaaa tgcatcaaat
 241 acctgctctt cgtcttcaat ttcgtcttct ggctggctgg aggcgtgatc ctaggtgtag
 301 ctctgtggtt gcgtcatgat ccacagacca ccagcctgct gtacctggaa ctgggaaaca
 361 aaccggcacc caacaccttc tacgtgggca tctacattct cattgctgtg ggagctgtga
 421 tgatgtttgt aggcttcctg gggtgctatg ggccatcca ggagtcccag tgtctgctgg
 481 ggacgttctt cacctgcctt gtgatcctgt ttgcctgtga ggtggctgca ggcatctggg
 541 gcttcgtaaa caagaccag atcgccaagg atgtgaagca gttctatgac caggccttc
 601 agcaagctgt gatggatgat gatgccaaca tgccaaggc tgtggtgaag actttccatg
 661 agacgctcaa ctgttgtggc tccaacgcac tgaccacact gactaccacc atactgagga
 721 acagcctgtg tccctcaggc ggcaacatac tcacccctt actgcagcaa gattgtcatc
 781 agaaaatcga tgagctcttc tctgggaagc tgtacctcat tggaattgca gccattgtgg
 841 tagctgtcat tatgatcttt gagatgattc tgagcatggt gctgtgctgt ggcatccgga
 901 acagctccgt gtactgaggc cctttgcatt gcaccagagg atccctggag tgaccagagg
 961 ccaccttggg ggacatggcc tgtgtatata atatttctgt atcactctgc tacacttagt
1021 ctttttactt ttgagttttt tgttttgttt tgtttgttt ttgttttagt ttttttttg
1081 tcctgaactt ttcctgttac cttttgggag ctgacatcac acatgggtgg catatgtggg
1141 atgtaggggt ggagctggcc ctggcttgca gggccctgta cgtctgggac ccctggagag
1201 ttctgcctgc tgagccaaac ctcctctaca gctacttgcc cagaggcttt gtagcctagc
1261 tagagggcca tgcccaccca ctcaacccac tgtgggtcac attgctcaca tctttttaat
1321 ctttgttcct ttcctgcctc catttcaaga gctgggtttg taagccctct tatgccttca
1381 atgcacttat tctttctaac gtgtcacctt caactgtaat taaatcttga aacagtcatt
1441 taataaagga ggaaaaaaat caggcaaaaa aaaaaaaaaa aaaaaaaaa aaaaaaaaa
1501 aaaaaaaaaa
```

Fig.6
wild
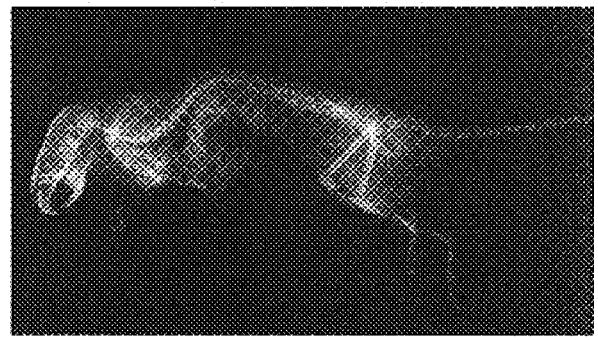
DKO
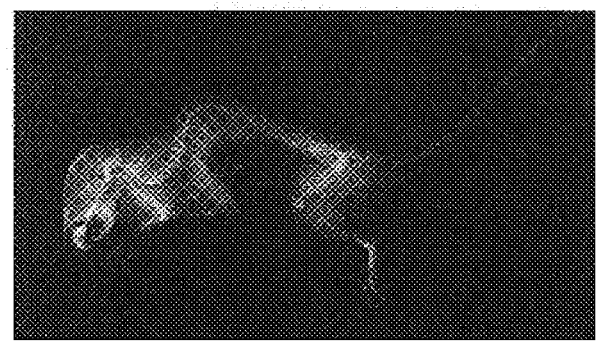
Fig.7
wild   DKO
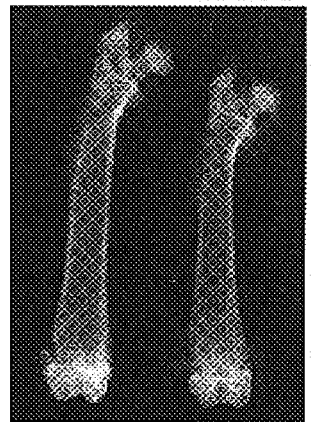

Osteoclast number (/100 mm)

Osteoclast surface (%)

Fig.12A
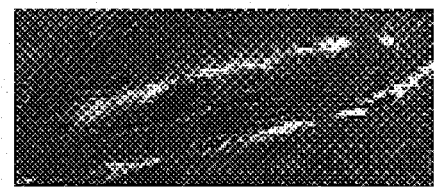
wild
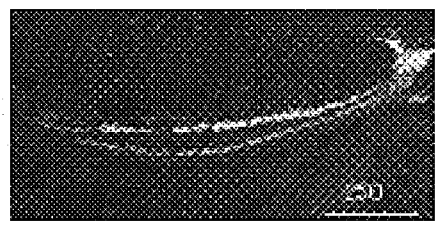
DKO

CD9/CD81 DOUBLE-DEFICIENT NON-HUMAN ANIMAL

CROSS-REFERENCE TO RELATED APPLICATIONS

This is a continuation of application PCT/JP2004/008261, filed on Jun. 7, 2004.

BACKGROUND OF THE INVENTION

1. Field of the Invention

The present invention relates to double-deficient non-human animals, in which CD9 gene and CD81 gene are deficient, that can be utilized as a model animal for development of therapeutic agents for osteoporosis or therapeutic agents for chronic obstructive pulmonary disease, etc.

2. Description of the Related Art

CD9 and CD81 are known as family members of protein called "tetraspanin". Tetraspanin is a superfamily, which, as shown by its name, has a structure spanning the cell membrane four times. Until now, about 30 members are known in mammals. Although the tetraspanin is considered to be related to proliferation, movement, and fusion of cells and infiltration and spread of cancer cells, etc., the detail of its function had been unknown. Recently, however, CD81 knockout mice (e.g. Maecker H T. J Exp Med 185:1505-1510, 1997) and CD9 knockout mice (e.g. Miyado K. Science 287: 321-324, 2000) were generated and showed abnormal antibody production and cytokine secretion, and infertility, respectively. Therefore, importance of tetraspanin in immune system and in genital system was revealed.

Osteoporosis is a disease, which mainly affects postmenopausal women and elderly people and causes pathological fracture and vertebral curvature. Therefore, there has been a demand for developing a more efficient therapeutic agent for osteoporosis, but there are not many experimental animal models for osteoporosis. At present, as an osteoporosis model animal, an ovariectomized mouse is often used, and this mouse is considered to be suitable as a model animal for osteoporosis with increased osteoclast activity due to reduced estrogen, which is common in postmenopausal women. On the other hand, as a mechanism of osteoporosis, so-called low-turnover type is also known in which the bone formation activity of osteoblasts is reduced, and a model animal that exhibits such low-turn over type is sought.

The relationship between osteogenesis by osteoblast and the tetraspanin had not been known at all.

Chronic Obstructive Pulmonary Disease (hereinafter may be referred to as "COPD"), which is an obstructive respiratory functional impairment, is comprised of two diseases: lung emphysema characterized by destruction of alveolar walls and enlargement of air spaces; and chronic bronchitis which involves persistent increase of respiratory secretions, and these two diseases often coexist. Its pathophysiology is abnormal inflammatory cell infiltration into the lung and production of proteolytic enzyme as a result of smoking.

Smoking is a major risk factor for COPD and the morbidity rate is increasing around the world. According to WHO, COPD is the fifth commonest cause of death at present and it is anticipated that it will be the third in 2020. However, its pathogenesis is still unclear. Only 15% to 20% of smokers develop COPD, and it is thought that sensitivity to smoking vary between individuals; however, there is not enough scientific support to demonstrate it.

Recently, it has been increasingly recognized that COPD patients not only have lung disease, but also frequently develop weight loss and muscle weakness and systemic complications such as osteoporosis, which accelerates the reduction of ADL and respiratory function (e.g. Biskobing D M. Chest 121:609-620, 2002). Administration of steroid drug, vitamin D deficiency, smoking, etc. are considered to be causes of these systemic changes, but mechanisms of these extrapulmonary effects are unknown.

Several genetically engineered mice have been produced in order to elucidate mechanisms of lung emphysema and to develop novel treatment strategies. For example, mice overexpressing the collagenase, one of proteinases, develop lung emphysema. Regarding knockout mice, models for lung emphysema are not many, although it is reported that mice such as surfactant protein D knockout and integrinβ knockout mice develop emphysema. (e.g. Wert S E. Proc Natl Acad Sci USA 97:5922-5977, 2000 and Morris D G Nature 422:169-173, 2003). Furthermore, these mice were not reported to develop extrapulmonary effects such as osteoporosis in addition to lung emphysema.

SUMMARY OF THE INVENTION

The invention aims to solve the conventional problems and to attain the following. The purpose of the invention is to provide a CD9/CD81 double-deficient non-human animal, which can be utilized as a model that exhibits a pathological condition resembling either osteoporosis or chronic obstructive pulmonary disease (COPD); and to provide a method to use the non-human animal model resembling either osteoporosis or COPD.

The inventors generated mice doubly deficient in CD9 and CD81, members of the tetraspanin protein family, and found that these mutant mice develop osteoporosis and COPD, thereby leading to the invention.

The means for attaining the aims of the invention are as follows.

<1> A CD9/CD81 double-deficient non-human animal, wherein functions of a gene coding for CD9 and a gene coding for CD81 are deficient at least in a somatic cell.

<2> The CD9/CD81 double-deficient non-human animal according to the <1>, wherein the non-human animal is a rodent animal.

<3> The CD9/CD81 double-deficient non-human animal according to the <2>, wherein the rodent animal is a mouse.

<4> The CD9/CD81 double-deficient non-human animal according to any one of the <1> to <3>, wherein the gene coding for CD9 is one of the following (a) and (b), and the gene coding for CD81 is one of the following (c) and (d):

(a) a DNA containing the base sequence described in SEQ ID NO: 1, (b) a DNA which hybridizes under a stringent condition with a DNA complimentary to the DNA containing the base sequence described in SEQ ID NO: 1, (c) a DNA containing the base sequence described in SEQ ID NO: 2, and (d) a DNA which hybridizes under a stringent condition with a DNA complimentary to the DNA containing the base sequence described in SEQ ID NO: 2.

<5> The CD9/CD81 double-deficient non-human animal according to any one of the <1> to <4>, wherein, in both a somatic cell and a germ cell, functions of the gene coding for CD9 and the gene coding for CD81 are deficient.

<6> The CD9/CD81 double-deficient non-human animal according to any one of the <1> to <4>, wherein at least one of the gene coding for CD9 and the gene coding for CD81 is introduced downstream of a promoter of a gene to be expressed specifically in a germ cell, and at least one of the functions of the gene coding for CD9 and the gene coding for CD81 is not deficient in the germ cell.

<7> The CD9/CD81 double-deficient non-human animal according to any one of the <1> to <6>, which displays at least one of a phenotype in which osteogenesis is inhibited and a phenotype similar to chronic obstructive pulmonary disease.

<8> The CD9/CD81 double-deficient non-human animal according to any one of the <1> to <7>, which is at least one of an osteoporosis model animal and a chronic obstructive pulmonary disease model animal.

<9> A method to use the CD9/CD81 double-deficient non-human animal of any one of the <1> to <7> as an osteoporosis model animal, including a step of measuring the degree of inhibition in the osteogenesis of the CD9/CD81 double-deficient non-human animal.

<10> The method according to the <9>, which is a method to screen a therapeutic agent for osteoporosis, wherein the method to screen a therapeutic agent for osteoporosis includes administering a test substance to the CD9/CD81 double-deficient non-human animal of any one of the <1> to <7>; and evaluating whether or not the test substance has an effect to reduce the inhibition of osteogenesis.

<11> A method to use the CD9/CD81 double-deficient non-human animal of any one of the <1> to <7> as a chronic obstructive pulmonary disease model animal, including a step of measuring the degree of a phenotype similar to chronic obstructive pulmonary disease of the CD9/CD81 double-deficient non-human animal.

<12> The method according to the <11>, which is a method to screen a therapeutic agent for chronic obstructive pulmonary disease, wherein the method to screen a therapeutic agent for chronic obstructive pulmonary disease includes administering a test substance to the CD9/CD81 double-deficient non-human animal of any one of the <1> to <7> to; and evaluating whether or not the test substance has an effect to reduce the phenotypic similarity to chronic obstructive pulmonary disease.

<13> A use of the CD9/CD81 double-deficient non-human animal of the <1> in order to generate at least one of an osteoporosis model animal and a chronic obstructive pulmonary disease model animal.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows a full-length DNA sequence of CD9 (SEQ ID NO: 1).

FIG. 2 shows a full-length DNA sequence of CD81 (SEQ ID NO: 2).

FIG. 6 is X-ray images of the whole body skeleton of a 30-week-old wild-type (wild) and CD9/CD81 double-deficient (DKO) mouse.

FIG. 7 is X-ray images of the femur of a 30-week-old wild-type (wild) and CD9/CD81 double-deficient (DKO) mouse.

FIG. 12A shows in vivo dual calcein labeling on an 8-week-old wild-type (wild) mouse and CD9/CD81 double-deficient (DKO) mouse.

DESCRIPTION OF THE PREFERRED EMBODIMENTS

Figure 3:
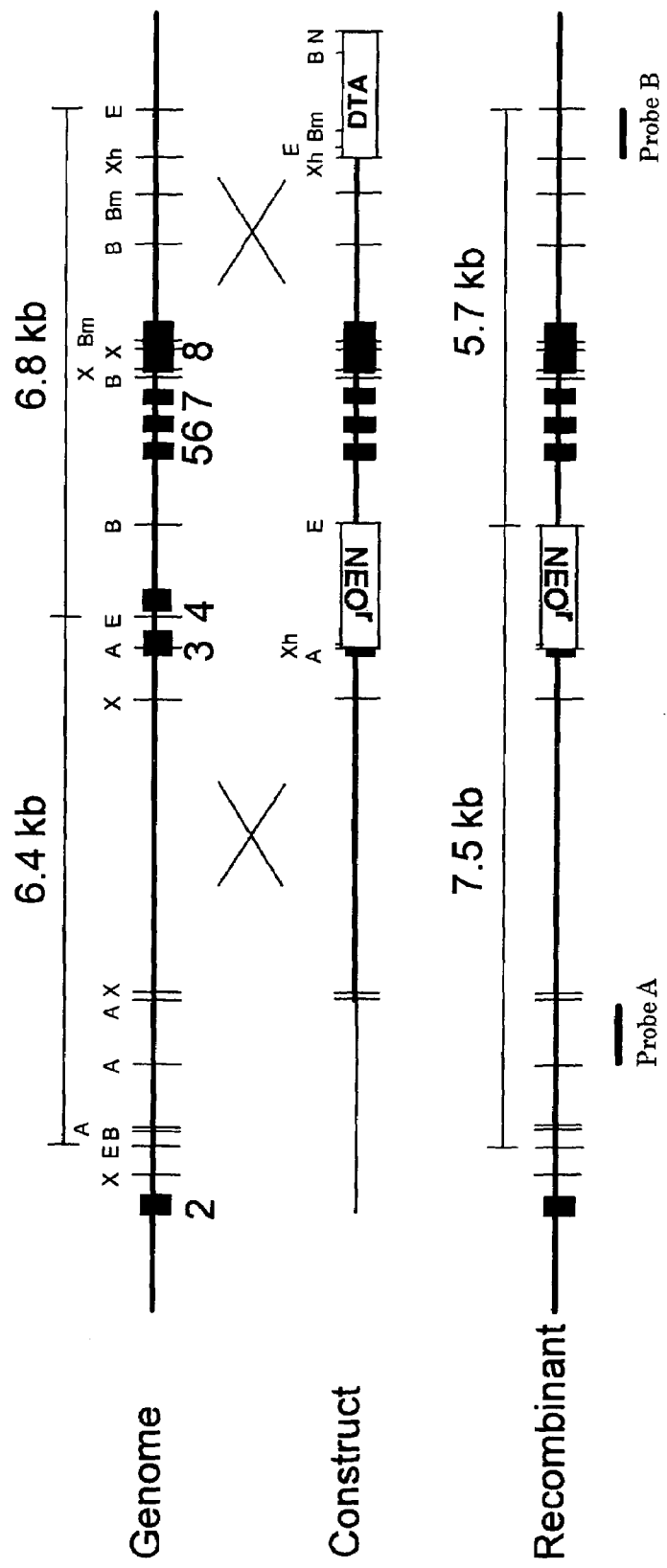
FIG. 3 shows a genomic DNA, construction vector, and recombinant DNA pertaining to a gene targeting for the generation of CD9 knockout mice.

The inventors for the first time generated mice deficient for both CD9 and CD81, members of the tetraspanin protein family, and found that these mutant mice develop osteoporosis. These CD9/CD81 double-deficient mice, compared with wild-type mice, showed small skeleton, kyphosis, thinning of cortical bone, and increased radiolucency of bone. From histomorphological analysis of the bone tissue, increase in osteoclast and decreased function thereof, and decreased function in osteoblast were suggested. Further, it was revealed that, by the in vivo dual labeling of calcein, the bone formation rate in the CD9/CD81 double-deficient mice was reduced to 60% of that in wild-type. Thus, the CD9/CD81 double-deficient mice show low-turnover type of osteoporosis and the CD9/CD81 double-deficient mouse can be a model for osteoporosis, which is one sign of human aging.

Inventors further found that this mutant mouse develops a pathological condition similar to human chronic obstructive pulmonary disease (COPD). The lung of the CD9/CD81 double-deficient mice was examined histologically, and it was observed that as the mice grow older, many inflammatory cells infiltrate in the alveolar walls, compared with wild-type mice, and air spaces were enlarged. Further, destruction or damage of elastic fiber of alveolar wall, and hyperplasia of bronchial mucus-producing cells were seen, which was consistent with a pathological condition of COPD in humans. Therefore, the CD9/CD81 double-deficient mouse can be a model of COPD.

In the non-human animal of the invention, functions of a gene coding for CD9 and gene coding for CD81 are deficient at least in somatic cells (In this description, it may be referred to as "CD9/CD81 double-deficient").

The non-human animal is not particularly limited as long as it is an animal other than humans. Examples of the non-human animal include mammals such as mice, rats, rabbits, pigs, dogs, sheep, and goats; birds such as chickens; and fishes such as trout; and mammals are preferred and rodents are more preferred. Among these, mice are particularly preferred in that they have short life cycle and breeding thereof is easy, and production technique of gene-deficient animal is established.

Here, "non-human animal in which function of a gene is deficient" refers to a non-human animal which has the gene whose function is deficient. Examples of the gene whose function is deficient include a gene whose expression is suppressed compared to a normal gene having no mutation, or a gene whose product has lost its activity or has a reduced activity. As long as this requirement is met, mutation includes not only deletion but also addition and substitution, and the site and length of mutation are not limited. Mutation can be introduced by any method without limitation, but can be introduced by a gene targeting method, in which DNA containing a base sequence of a target gene into which mutation is introduced, is introduced into cells, and cells in which homologous recombination has occurred are selected, thereby introducing mutation into a target gene. The targeting site into which mutation is introduced may be any site including, for example, a promoter region, untranslated region, coding region. For example, a mutated gene whose transcription activity has been impaired can be obtained by deletion or substitution in the base sequence of the promoter region of a gene. Further, a mutated gene, in which a stable transcription product has not been synthesized as a result of deletion or substitution in the base sequence of the untranslated region, can also be obtained. Further, a mutated gene can be obtained whose product cannot be obtained or, even if the gene product is obtained, it does not function normally as a protein, as a result of deletion or substitution in the base sequence within the coding region. In order to make a gene function fully defective efficiently, preferable targeting site is the coding region. Further, selection markers such as a resistance gene for agents are preferably introduced into a gene to be introduced from the viewpoint that recombinants of interest can be easily selected. Here, "functions of a gene coding for CD9 and gene coding for CD81 are deficient" means that both the function of the gene coding for CD9 and the function of the gene coding for CD81 are deficient, mainly referring to so-called double-knockout.

Further, the non-human animal of the invention may be those in which a mutated gene, whose function is deficient, is present in a homologous state on chromosomes (homozygote), or may be those in which the mutated gene is present in a heterologous state on chromosomes (heterozygote). The heterozygote can be utilized mainly for breeding of homozygote.

Here, it is known that the gene coding for CD9 is present, for example, in a salmon (AF427519), chicken (AB032767), mouse (NM__007657), rat (XM__216279), cat (D30786), dog (U15792), pig (AF525029), cattle (NM__173900), monkey (D10726), and human (NM__001769), and it is known that the gene coding for CD81 is present, for example, in zebra fish (NM__131518), chicken (AB101638), mouse (NM__133655), rat (NM__013087), monkey (AF116600), and human (NM__004356). The number in parentheses is a Genbank accession number, and this number allows to access to the base sequence information of a gene and amino-acid sequence information of the protein for which the gene codes. For example, in a mouse, as previously reported, the base sequence of the gene coding for CD9 is described in SEQ ID NO: 1 (FIG. 1) and the base sequence of the gene coding for CD81 is described in SEQ ID NO: 2 (FIG. 2). Further, the amino-acid sequence of the CD9 protein of mouse is shown in SEQ ID NO: 10, and amino-acid sequence of the CD81 protein in SEQ ID NO: 11.

```
SEQ ID NO: 10:
mpvkggskci kyllfgfnfi fwlagiavla iglwlrfdsq
tksifeqenn hssfytgvyi ligagalmml vgflgccgav
qesqcmlglf fgfllvifai eiaaavwgyt hkdevikelq
efykdtyqkl rskdepqret lkaihmaldc cgiagpleqf
isdtcpkkql lesfqvkpcp eaisevfnnk fhiigavgig
iavvmifgmi fsmilccair rsremv SEQ ID NO: 11:
mgvegctkci kyllfvfnfv fwlaggvilg valwlrhdpq
ttsllylelg nkpapntfyv giyiliavga vmmfvgflgc
ygaiqesqcl lgtfftclvi lfacevaagi wgfvnkdqia
kdvkqfydqa lqqavmddda nnakavvktf hetlnccgsn
alttltttil rnslcpsggn iltpllqqdc hqkidelfsg
klyligiaai vvavimifem ilsmvlccgi rnssvy
```

Further, the gene coding for CD9 and gene coding for CD81 are not limited to those having the sequences previously reported, even in the animals other than those mentioned above, the gene coding for CD9 is present as a DNA which hybridizes under stringent conditions with a DNA complimentary to a DNA containing the base sequence described in SEQ ID NO: 1, and the gene coding for CD81 is present as a DNA which hybridizes under stringent conditions with a DNA complimentary to a DNA containing the base sequence described in SEQ ID NO: 2. Here, examples of the stringent condition include hybridization in 4×SSC at 65° C., followed by washing in 0.1×SSC at 65° C. for one hour. Further, the gene coding for CD9, of the animal other than those mentioned above, include, for example, genes coding for the protein having amino-acid sequence in which one or plural, preferably, one or several amino acid residues are added, deleted, or substituted in the amino-acid sequence SEQ ID NO: 10) of protein for which DNA containing the base sequence described in SEQ ID NO: 1 codes. Similarly, the gene coding for CD81, of the animal other than those mentioned above, include, for example, genes coding for the protein having amino-acid sequence in which one or several amino acid residues are added, deleted, or substituted in the amino-acid sequence (SEQ ID NO: 11) of protein for which DNA containing the base sequence described in SEQ ID NO: 2 codes.

The non-human animal of the invention is one in which the functions of the gene coding for CD9 and gene coding for CD81 are deficient, and it would be enough if this "deficiency in the functions" have taken place at least in somatic system. Specifically, the invention does not exclude even such a case, for example, where the functions of the CD9 gene and CD81 gene from the non-human animal are deficient, and a gene coding for CD9 and/or gene coding for CD81, which are newly introduced under a promoter not to be expressed under normal condition in somatic cells, are present. The non-human animal may be a transgenic mouse in which CD9 and CD81 are introduced under the promoter to be expressed specifically in germ cells.

Specifically, by a normal gene targeting technique as described later, non-human animals, in which recombination has occurred in all cells including germ cells and target proteins having function are not expressed in all cells, can be obtained. However, since CD9 gene deficient female mice are infertile, normally in order to obtain this mouse, it is necessary to generate mice by mating of heterozygotes with each other or by mating between heterozygous female and CD9 gene deficient male mice. Further, it is known that CD81 gene deficient female mice also generate a small number of offspring, and certain strain of mice become infertile. Therefore, in order to generate CD9/CD81 double-deficient homozygous mice by present technology, it is most efficient to obtain by mating between CD9/CD81 double-deficient male mice and CD9/CD81 double-deficient heterozygous female mice. However, the rate of the birth of CD9/CD81 double-deficient homozygous mice is 25% and therefore, it is disadvantageous to produce a large amount of CD9/CD81 double-deficient homozygous mice which are useful as an experimental model mouse. The reason why the CD9 gene deficient female mice are infertile is that CD9 is expressed in ovum and is essential when the ovum is fertilized with a sperm. However, once fertilization is completed, CD9 is not required in the following developmental processes, and it is revealed that even mice not having CD9 generate fetuses. The invention also includes CD9/CD81 double-deficient mice, in which at least CD9 is introduced under the promoter to be expressed selectively in germ cells (CD81 may also be introduced), which was invented so that homozygous females and males can be mated. Similarly, the invention does not exclude CD9/CD81 double-deficient mice, in which CD81 is introduced under the promoter to be expressed selectively in germ cells.

The CD9/CD81 double-deficient mice, as mentioned above, in which CD9 and/or CD81 is introduced under the promoter to be expressed specifically in germ cells can, for example, be generated as follows. Transgenic mice (TG-Pzp3::CD9) are generated in which CD9 structural gene is introduced downstream of the promoter of ZP3 gene which is a gene to be expressed specifically in ovum, and then, the TGPzp3::CD9 are mated with CD9 gene deficient mice to generate mice which do not have a CD9 gene but have a Pzp3::CD9 gene. The obtained mice express CD9 in ovum and could generate offspring.

In this way, by using a technique in which a CD9 gene is introduced downstream of the promoter of the gene to be expressed specifically in ovum, such as ZP3, the function of CD9 gene is deficient and CD9 is not expressed in somatic cells, thus, the obtained mice have a property of CD9 gene deficient mice. In addition, use of the technique enables mating between homozygous females and males, and is very advantageous for producing a large amount of CD9 gene deficient mice and CD9/CD81 double-deficient mice.

The CD9/CD81 double-deficient mice, which is generated by mating the thus-obtained CD9 deficient mice with CD81 deficient mice obtained by a normal method, have a newly introduced CD9 (TGPzp3::CD9) both in germ cells and somatic cells, but do not express CD9 in somatic cells in a normal condition. Thus, it can not be said that the CD9/CD81 double-deficient mice express functional CD9, but can be said that CD9 becomes deficient at least in somatic system. Therefore, such mice are also included within the scope of the invention.

It is considered that the reason why CD81 deficient female mice are likely to be infertile is, likewise, because CD81 is required in the process of fertilization, and it can be solved in the same way as the CD9 gene deficient mice. Such CD9/CD81 double-deficient mice expressing CD9, or CD9 and CD81 downstream of ZP 3 gene promoter are advantageous in that mating between the CD9/CD81 double-deficient homozygous female and male mice is possible and the CD9/CD81 double-deficient mice are easily generated in large amounts as a model mouse.

In the CD9/CD81 double-deficient animal of the invention, homozygote displays decreased osteogenesis (phenotype in which osteogenesis is inhibited). This is evidenced either by the reduction in the rate of osteogenesis, which is measured by the calcein labeling, or by the decrease in bone formation parameters (osteoid thickness, osteoid surface, and osteoblast surface), which is determined by histomorphometry, compared with wild-type, at least in a part of bone tissues.

Further, in the CD9/CD81 double-deficient animal of the invention, homozygote displays a phenotype similar to human COPD. The phenotype similar to COPD includes, for example, infiltration of inflammatory cells and enlargement of air spaces in the alveolar walls of the lung of an aged non-human animal. When the lungs of the CD9/CD81 double-deficient mice are histologically analyzed and compared with wild-type mice, it is observed that with aging, many inflammatory cells infiltrate in the alveolar walls and air spaces are enlarged. These correspond to the histological characteristic of lung emphysema in human COPD. Further, destruction or damage of elastic fiber of alveolar wall, and hyperplasia of bronchial mucus-producing cells are seen. This is consistent with a pathological condition of COPD in humans.

The non-human animal can be utilized as either an osteoporosis model animal or a COPD model animal.

The method for using the non-human animal as an osteoporosis model animal comprises a step of measuring the degree of inhibition in the osteogenesis of the non-human animal of the invention. The method for measuring inhibition of osteogenesis is not particularly limited as long as it is related to osteogenesis, and can be appropriately selected from known methods, including an assay by the calcein labeling and histomorphometry of bone formation parameters (osteoid thickness, osteoid surface, and osteoblast surface), and bone resorption parameters, in addition to, a measurement of actual bone mass.

Further, examples of the method for using the non-human animal as an osteoporosis model animal include screening therapeutic agents for osteoporosis. Effective medical agents can be screened by administering a test substance, which is a candidate compound of medical agent to the non-human animal, by measuring the degree of the inhibition of bone formation, and by evaluating whether or not the test substance has an effect to reduce the inhibition of osteogenesis.

The test substance may be administered in any form without limitation, for example, orally, by injection, by application or the like.

The method to use the non-human animal as a COPD model animal comprises a step of measuring the degree of a phenotype similar to chronic obstructive pulmonary disease in the CD9/CD81 double-deficient non-human animal of the invention. Examples of the method to measure the phenotype include the evaluation of infiltration of inflammatory cells and enlargement of air spaces in the alveolar walls by histological analysis of the aged non-human animal. Evaluation of elastic fiber destruction in the alveolar wall and bronchial mucus-producing cells by histological analysis is also included. Furthermore, the measurement of increase in the number of macrophage and in the activities of matrix metalloproteinases (MMPs) (especially, MMP-2 and MMP-9) of the bronchoalveolar lavage fluid is also included.

Examples of the method for using the non-human animal as a COPD model include a method to screen therapeutic agents for chronic obstructive pulmonary disease. Effective medical agents can be screened by administering a test substance, which is a candidate compound of medical agent, by measuring the degree of the COPD phenotype, and by evaluating whether or not the test substance has an effect to reduce the phenotype similar to chronic obstructive pulmonary disease.

The method for producing the CD9/CD81 double-deficient non-human animal is not particularly limited and can be any known method. For example, double-deficient mice can be generated out as follows.

The CD9 gene is isolated and a targeting vector containing a mutated gene sequence in which part of the CD9 gene is replaced with a genetic marker is prepared. This targeting vector is introduced into mouse embryonic stem cells (ES cells), allowing homologous recombination with a CD9 gene. ES cells which have undergone homologous recombination are obtained using a genetic marker as an index. The mouse ES cells, which have undergone homologous recombination, are microinjected into fertilized eggs, which are implanted into the uterus of pseudopregnant female mice, and allowed to develop to adult chimeric mice. The male chimeric mice are selected and mated with wild-type female mice. From the offspring, heterozygote mice between the chimeric and wild type mice, in which CD9 deficient gene derived from the ES cells is taken into the germ line, are selected based on the coat colors, etc. The heterozygote mouse line of CD81 can be similarly obtained. A CD9 deficient heterozygote is mated with a CD81 deficient heterozygote to obtain the CD9/CD81 double-deficient mice.

The invention will be described specifically below with reference to Examples, which are not intended to limit the scope of the invention. In the Examples, all mice were bred under the specific pathogen-free conditions in an environmentally controlled clean room of the Institute of Experimental Animal Sciences, Osaka University Medical School. All instruments and foods including a cage, water bottle, woodchip, and pellet or feed grain were sterilized.

Example 1

Generation of CD9/CD81 Genes Double-Deficient Mice (Double Knockout Mice (Step 1) Cloning of Genomic DNA of the CD9 Gene and Generation of CD9 Deficient Mice Genomic DNA of mouse CD9 was isolated from a 129/sv mouse genomic phage library purchased from Stratagene Corporation using a full-length cDNA (SEQ ID NO: 1) as a probe. About $9 \times 10^5$ phage clones were screened by plaque hybridization, and 20 positive clones were obtained. In order to confirm whether or not these clones coded for CD9, the second screening was carried out using a CD9 probe. As a result, it was found that all clones were CD9 positive clones derived from a single phage clone. For the obtained clones, a restriction map of genomic clone was made by the digestion of genomic clone with several restriction enzymes and by partial sequencing (FIG. 3). The obtained CD9 clones covered 60 kb of the gene and contained homologous sequence corresponding to the exons 1 to 6 of the human CD9 gene.

(Step 2) Construction of CD9 Targeting Vector

Targeting strategy of CD9 gene is shown in FIG. 3. In order to prepare a targeting vector for the CD9 gene, a positive selection marker gene (neo-polyA cassette) was inserted into the isolated genome by replacing a part of the gene by using restriction enzymes.

The targeting vector of CD9 gene was constructed as follows. A ca. 1.3 kb DNA fragment between ApaI and BamHI sites of exons 3 and 4, which corresponded from the second transmembrane domain to the fourth transmembrane domain of mature CD9, was replaced with neo-polyA cassette. Next, diphtheria toxin A fragment gene (DT) as a negative marker was inserted at 3' end of the vector under the control of thymidine kinase promoter (FIG. 3). The homologous regions at 5' and 3' ends were about 4 kb and 5 kb, respectively.

(Step 3) Preparation of Targeting Vector-Integrated ES Cells

The ES cells for use in the invention are TT2 cells obtained from C57BL6+CBA mouse. TT2 cells can be obtained in such a way as described by Dr. Shinichi Aizawa (Jikken Igaku separate volume bio manual series 8, "Gene Targeting", preparation of mutant mouse using ES cells, Yodosha, 1995). By electroporation of ES cells, about 20 μg to 25 μg of the linearized targeting vector was transfected into $10^7$ ES cells. The electroporation can be carried out, for example, with the Bio-Rad Gene Pulser at 250 V and 500 μF. Next, cells were cultured in ES medium (Dulbecco's modified Eagle medium (Nacalai Tesque, Inc.) supplemented with 20% bovine fetal serum (Sigma), murine leukemia inhibitory factor (LIF) (ES-GRO, Amrad Corporation Limited), sodium pyruvate (Nacalai Tesque, Inc.), nonessential amino acid (Wako Pure Chemical Industries, Ltd), and β-mercaptoethanol (Nacalai Tesque, Inc.)) using neomycin (200 μg/ml, Sigma) as a selectable agent. The selective medium was exchanged every day.

One hundred and sixteen ES clones that grew in the presence of neomycin were pooled and genomic DNA was isolated therefrom. In order to confirm whether homologous recombination occurred, clones were screened by the Southern blot hybridization method. Using an ApaI-ApaI fragment as a 5' probe (probe A in FIG. 3), and a XhoI-EcoRI fragment as a 3' probe (probe B in FIG. 3), the targeted CD9 gene was analyzed by southern blot hybridization. The genomic DNA obtained from ES cells was digested with HindIII, electrophoresed on a 0.5% agarose gel, and transferred to a nylon membrane (Amasham). Hybridization was carried out in hybridization buffer (Toyobo) with $^{32}$P-labeled probes A and B at 68° C. The membrane was washed, exposed to the film, and analyzed.

Figure 4:
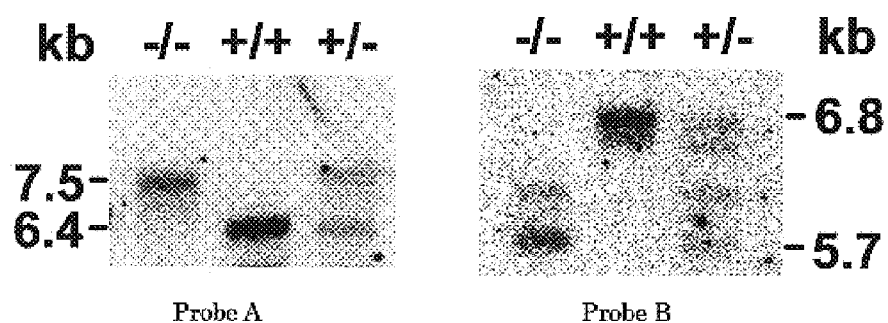
FIG. 4 shows a result of CD9 Southern blot.

By southern hybridization, 6.4 kb (probe A) and 6.8 kb (probe B) bands, which corresponded to bands derived from CD9 wild-type allele; and 7.5 kb (probe A) and 5.7 kb (probe B) bands, which corresponded to bands derived from the mutated allele, were detected (FIG. 4). This showed that one of wild-type alleles to be targeted in ES clones was properly substituted with the mutated gene. The targeting efficiency of the CD9 gene was 6.0%. Among these, the introduction of the gene to be targeted into germ line was confirmed in two clones out of two clones.

(Step 4) Generation of CD9 Gene Deficient Mice

ES cells in which CD9 gene was targeted were implanted in a fertilized embryo. The implanting method can be appropriately modified by those skilled in the art, and, in this example, chimeric embryos were generated by an injection method into eight-cell stage embryos, which was modified from the method originally reported (Nagy et al., 1993, Proc. Natl. Acad. Sci. USA 90, 8424-8428). Specifically, in a hole on a plastic dish, ES cells were placed between the zona pellucida and blastomere of eight-cell stage embryos in which compaction has not occurred, and cultured overnight in a BBM medium or M16 medium. Then, fully formed blastula was implanted into the uterus of a pseudopregnant female mouse (Hogan et al. Manipulating the mouse embryo, Cold Spring Harbor Laboratory Press, 1994). The strain, from which an embryo that can be used as an eight-cell stage embryo in the injection method is derived, may be from mating between pure lines, or may be from mating within the pure line. In the invention, it is desirable to use an embryo derived from F1 of the ICR strain.

After male chimeric mice derived from the embryo, into which ES cells were introduced, matured, this mice were mated with female mice from pure line mice lineage, and by the coat color of offspring, introduction of ES cells into the germ line of the chimeric mouse was confirmed. In this Example, as mentioned above, since ES cells derived from agouti strain (TT2) were used, the generated male chimeric mice were mated with C57BL6 female mice, black color, and by the fact that the coat color of next generation progeny was agouti+(black), introduction of ES cells into the germ line of the chimeric mouse was confirmed. By mating of the obtained CD9 gene deficient heterozygous mice with each other, CD9 gene deficient homozygous mice of interest could be obtained.

(Step 5) Genotype Analysis

In the progeny of the CD9 gene deficient mice generated in this Example, heterozygotes were healthy and had reproductive capacity. The mice obtained by mating of heterozygotes with each other were screened by examining whether or not the mice have an allele in which homologous recombination was occurred by PCR using DNA isolated from their tails. In the PCR reaction, the following primers, SEQ ID NOs: 3 to 5, were used.

```
                                            (SEQ ID NO: 3)
P1:  5'-AATGGGCTGACCGCTTCCTCG-3'

(SEQ ID NO: 4)
P2:  5'-CCTCCCTCAGGAGTGTACATTC-3'

(SEQ ID NO: 5)
P3:  5'-GAGGAACCCGAAGAACTAGAAGAC-3'
```

Figure 5:
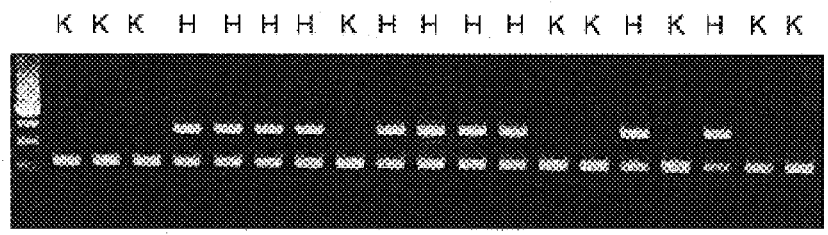
FIG. 5 shows a result of CD9 PCR.

The primers indicated as SEQ ID Nos: 3 and 4 were used for the detection of deficient allele, and the primers indicated as SEQ ID Nos: 4 and 5 for the detection of wild-type allele. PCR reaction buffer contained 50 mM Tris-HCl (pH 8.0), 0.1 mM EDTA, 1 mM DTT, 0.001% Tween 20, 0.001% NP-40, 50% glycerol, 25 mM MgSO$_4$, 2 mM dNTP, and 1 U/il polymerase (KOD Plus Toyobo). PCR was carried out for 30 cycles, and each cycle consisted of 94° C. for 15 seconds, 62° C. for 30 seconds and 68° C. for 1 minute. As shown in FIG. 5, it was confirmed that the heterozygotes (H) had both an allele in which recombination has occurred, and a wild-type allele, and the homozygotes (K) had only the allele in which recombination has occurred. Furthermore, it was found that homozygotes came out according to Mendelian ratio by mating of heterozygotes with each other.

(Step 6) Construction of CD81 Targeting Vector

CD81 targeting vector was prepared according to the method described in "Miyazaki, T. et al. (1997) The EMBO Journal Vol. 16, pp 4217-4225". Briefly, in order to prepare the targeting vector of CD81 gene, part of DNA fragment of an isolated genomic clone was deleted with restriction enzyme, and a positive selection marker gene (neo-polyA cassette) was inserted at the same site.

Specifically, the region containing all of exons 3 to 7 and part of exon 8, i.e., an about 3 kb DNA fragment containing from part of the second transmembrane domain to C terminus of a mature CD81 was deleted with restriction enzyme BamHI, and the neo-polyA cassette was inserted in stead of the DNA fragment (Information of introns and exons of CD81 can be found under the accession number AJ251835).

ES clones which grew in the presence of neomycin were stocked, and then genomic DNA was isolated. In order to confirm whether or not homologous recombination has occurred, the clones were screened by a southern hybridization method.

(Step 7) Generation of CD81 Gene Deficient Mice and Genotype Analysis CD81 gene deficient mice were generated in the same way as in CD9. In the progeny of the CD81 gene deficient mice generated, heterozygotes were healthy and had reproductive capacity. The mice obtained by mating of heterozygotes with each other were screened by examining whether or not the mice have an allele in which homologous recombination was occurred by PCR using DNA isolated from their tails. In the PCR reaction, the following primers, SEQ ID NOs: 6 to 9, were used.

```
                                            (SEQ ID NO: 6)
P1:  5'-TGTGAGGTGGCTGCAGGCATCTGG-3'

(SEQ ID NO: 7)
P2:  5'-TCTCATGGAAAGTCTTCACCACAG-3'

(SEQ ID NO: 8)
P3:  5'-GTATCCATCATGGCTGATGCAA-3'

(SEQ ID NO: 0)
P4:  5'-AGCTCCACCCCTACATCCCAC-3'
```

The SEQ ID NOs: 6 and 7 were used for the detection of wild-type allele, and SEQ ID NOs: 8 and 9 for the detection of deficient allele.

The generation of CD81 knockout mice is described in "Maecker H T, Levy S. J Exp Med. 1997 Apr. 21; 185(8): 1505-10. Normal lymphocyte development but delayed humoral immune response in CD81-null mice.", which was mentioned as Non-Patent Literature 1, and also in "Tsitsikov E N, Gutierrez-Ramos J C, Geha R S. Proc Natl Acad Sci U S A. 1997 Sep. 30; 94(20):10844-9. Impaired CD19 expression and signaling, enhanced antibody response to type II T independent antigen and reduction of B-1 cells in CD81-deficient mice.".

(Step 8) Generation of CD9/CD81 Genes Double-Deficient Mice

By mating of CD9 gene deficient mice (heterozygotes) with CD81 gene deficient mice (heterozygotes), CD9/CD81 genes double-deficient heterozygous mice were generated. Further, by mating between CD9/CD81 genes double-deficient heterozygous female and male mice, CD9/CD81 genes double-deficient homozygous mice were generated.

Example 2

Figure 8:
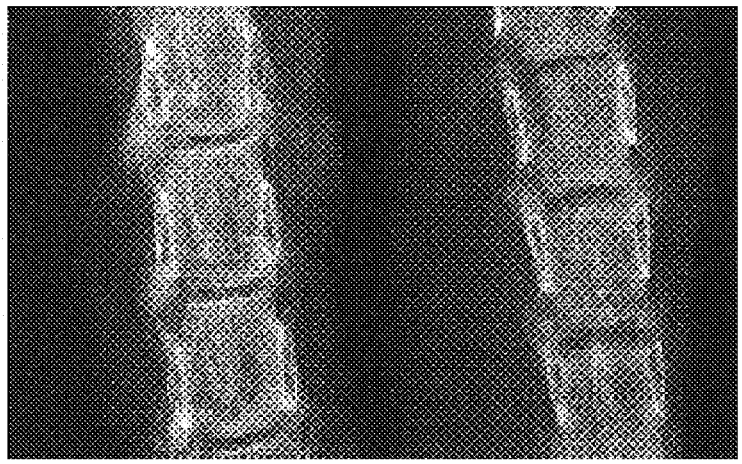
FIG. 8 is X-ray images of the vertebra of a 30-week-old wild-type (wild) and CD9/CD81 double-deficient (DKO) mouse.

The bones of 30-week-old mice were subjected to X-ray photography. After mice were anesthetized, X-ray photography was carried out using micro-FX1000 (Fuji Film, Inc.). X-ray images of whole body skeleton, femur, and vertebra are shown in FIGS. 6, 7, and 8, respectively. In the CD9/CD81 double-deficient (DKO) mice, compared with wild-type (wild type) mice, the skeleton was smaller and kyphosis was observed. Further, the bones were more radiolucent, indicating the loss of bone mineral density. The CD9/CD81 double-deficient mice used in this Example and Examples below were homozygotes.

Example 3

8-week-old mice were used for examining proximal tibiae histologically. The tibiae of 8-week-old wild-type and CD9/CD81 double-deficient mice were fixed with 90% ethanol and undecalcified specimens were embedded in glycomethacrylate. 3 mm wide sections of proximal tibiae were stained with toluidine blue or TRAP.

Figure 9:
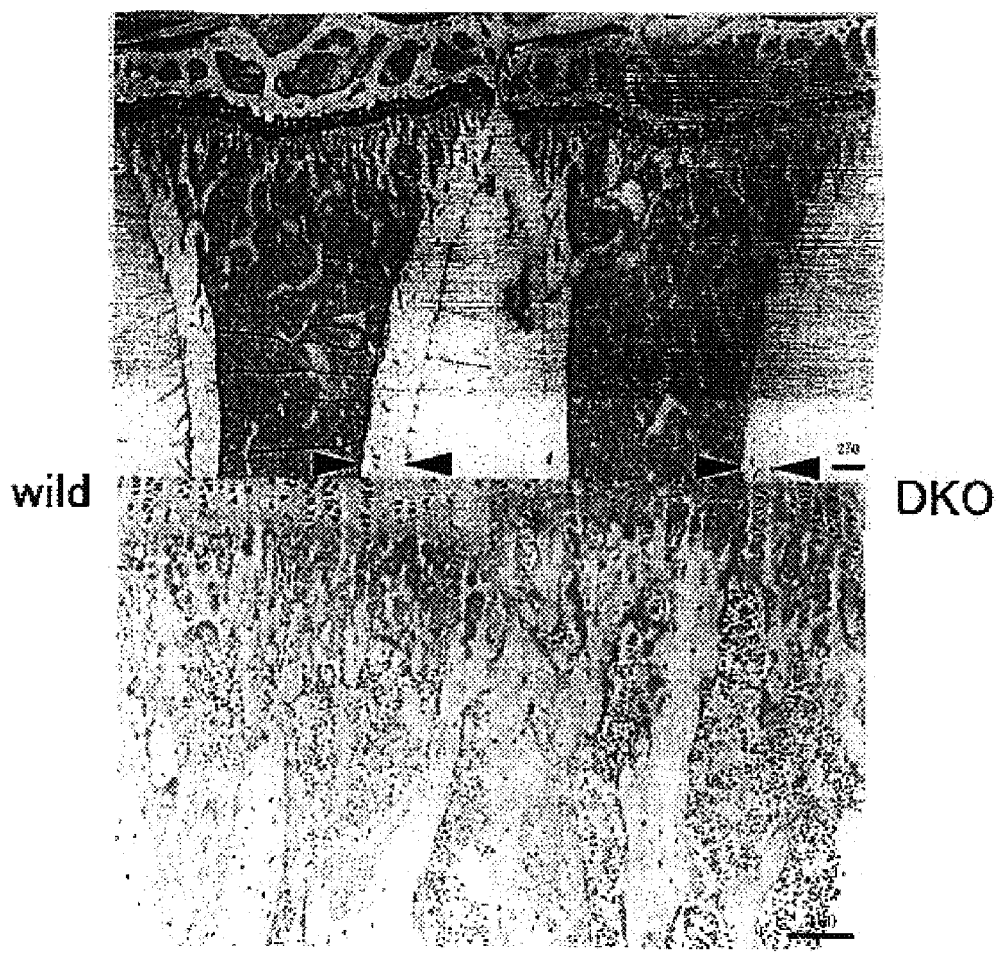
FIG. 9 shows tissue sections of the proximal tibia of an 8-week-old wild-type (wild) and CD9/CD81 double-deficient (DKO) mouse, in which the upper is staining with toluidine blue and the lower is staining with TRAP.

The sections stained with toluidine blue and with TRAP are shown in the upper part and lower panels of FIG. 9, respectively. Left and right panels indicate the specimens of wild-type and CD9/CD81 double-deficient mice, respectively, and in the upper part of FIG. 9, Bar=250 μm, in the lower part of FIG. 9, Bar=100 ||m.

In the upper part of FIG. 9, the arrowheads represent cortical bone. The cortical bone was thinner in the CD9/CD81 double-deficient mice when compared with wild-type. In the TRAP staining, osteoclasts are strongly stained in red.

Example 4

Figure 10A:
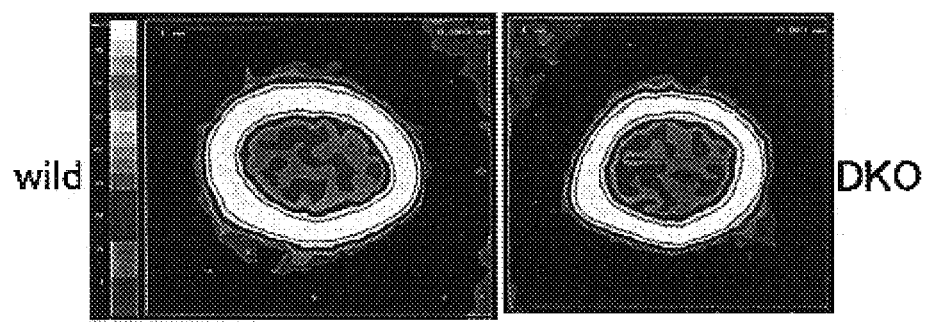
FIG. 10A represents pQCT images of the femur of an 8-week-old wild-type (wild) and CD9/CD81 double-deficient (DKO) mouse.
Figure 10B:
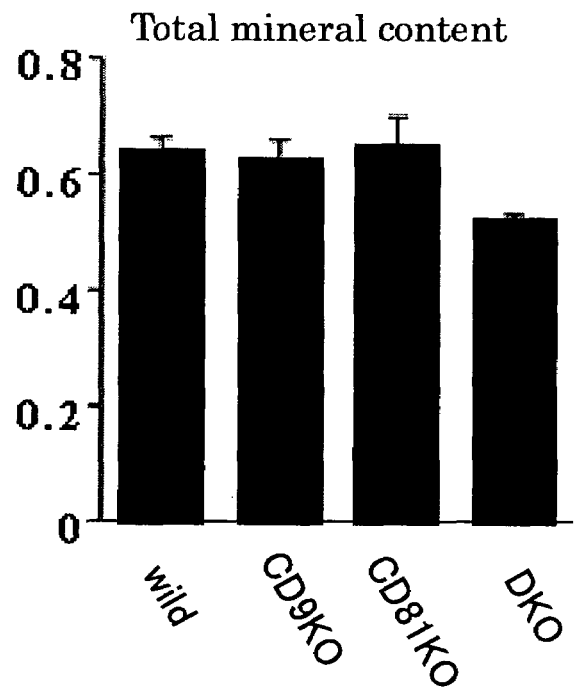
FIG. 10B represents total mineral content of the femur of an 8-week-old wild-type (wild), CD9 deficient mice, CD81 deficient mice, and CD9/CD81 double-deficient (DKO) mice.
Figure 10C:
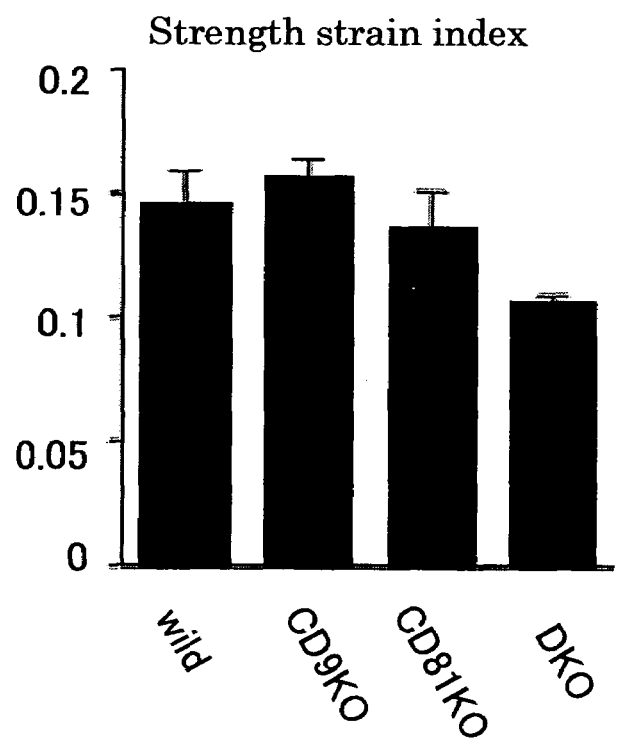
FIG. 10C represents strength strain index of the femur.

Femurs of 8-week-old wild-type mice, CD9/CD81 double-deficient mice, CD9 deficient mice and CD81 deficient mice were analyzed by peripheral quantitative computed tomography (pQCT) analysis. The pQCT analysis was carried out as follows: the femurs of the mice were fixed with 10% formalin, and then measured using XCT research SA (Stratec Medizintechnik). The contour of the total bone was determined automatically by the pQCT software algorithm. Results of analysis are shown in FIGS. 10A to 10C. When compared with wild-type mice, CD9 deficient (KO) mice, and CD81 deficient (KO) mice, total mineral content and strength strain index were decreased in the CD9/CD81 double-deficient (WKO) mice. The results of Examples 2 and 4 indicate that the bone mineral density was decreased in the CD9/CD81 double-deficient mice.

Example 5

Histomorphometry of the proximal tibiae of the following 8-week-old mice was carried out: wild-type (Wild), CD9 deficient (CD9KO) mice, CD81 deficient (CD81KO) mice, CD9/CD81 double hetero (CD9/CD81DHO) mice and CD9/CD81 double-deficient (CD9/CD81 DKO) mice. Results of triplicate samples of proximal tibia from each mouse were analyzed by Osteoplan II (Zeiss) semi-automation system and shown in FIGS. 11A to 11H.

No decrease in trabecular bone volume, trabecular thickness, and trabecular number was seen, indicating that trabecular bone was intact in the CD9/CD81 double-deficient mice (FIGS. 9, and 11A to 11C).

Figure 11A:
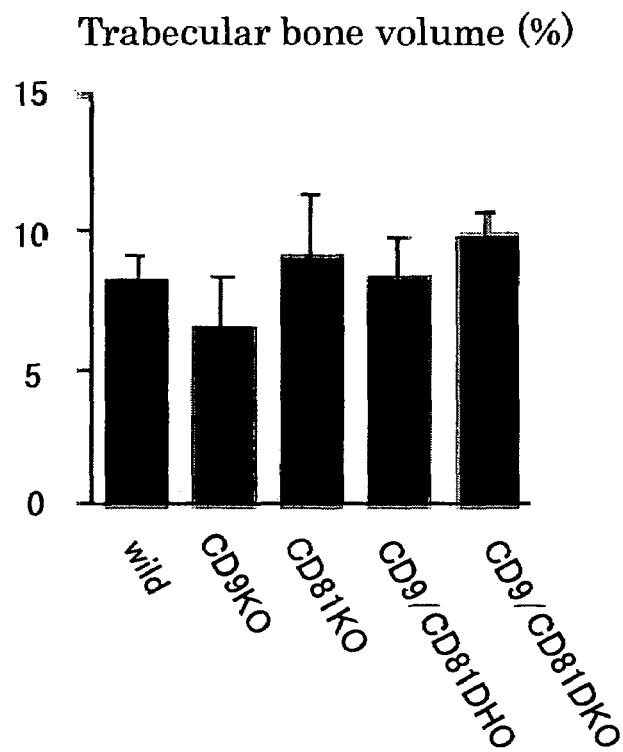
FIG. 11A shows trabecular bone volume (BV/TV) determined in histomorphometric analysis of the proximal of an 8-week-old wild-type, CD9 deficient (CD9 KO) mice, CD81 deficient (CD81KO) mice, CD9/CD81 double hetero (CD9/CD81DHO) mice and CD9/CD81 double-deficient homo (CD9/CD81 DKO) mice. The parameter is shown according to the recommended ASBMR (American Society for Bone and Mineral Research) standards.
Figure 11B:
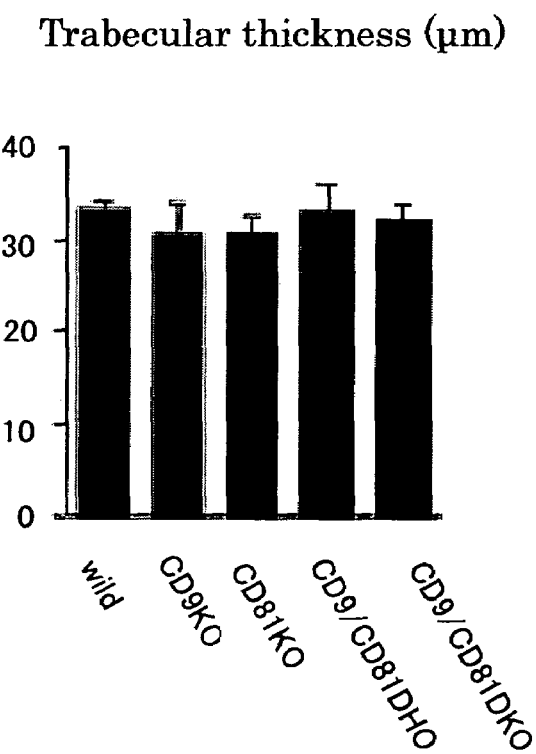
FIG. 11B shows trabecular thickness (Tb.Th) determined as in FIG. 11A.
Figure 11C:
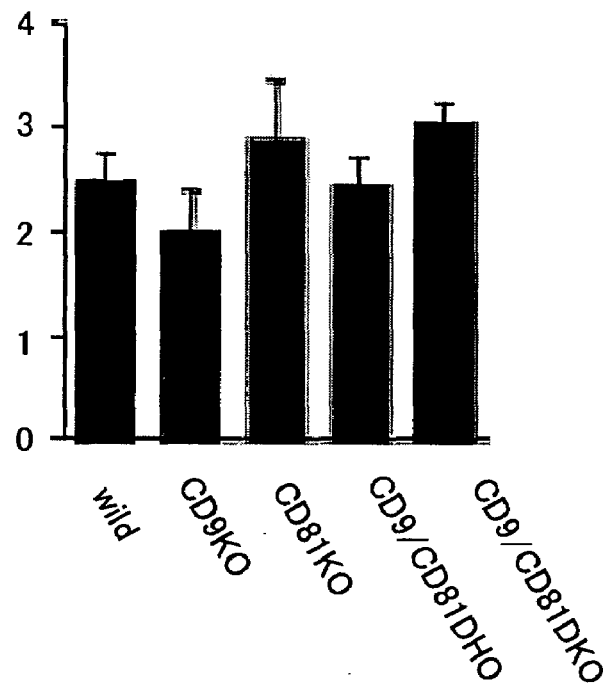
FIG. 11C shows trabecular number (Tb.N) determined as in FIG. 11A.
Figure 11D:
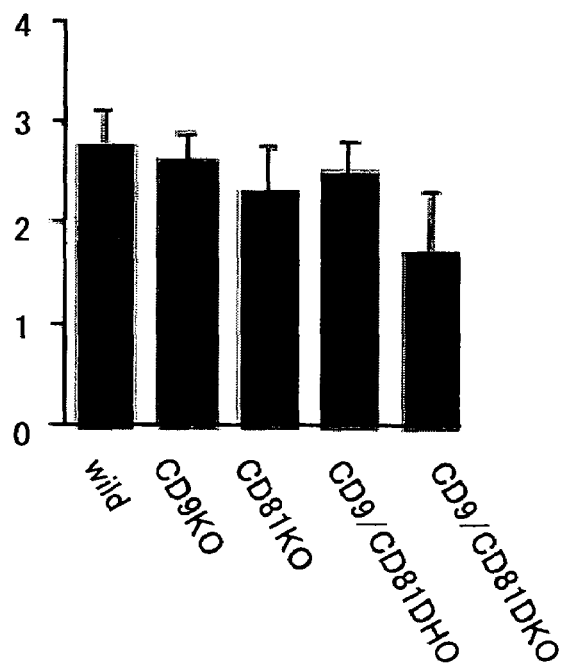
FIG. 11D shows osteoid thickness (O.Th) determined as in FIG. 11A.
Figure 11E:
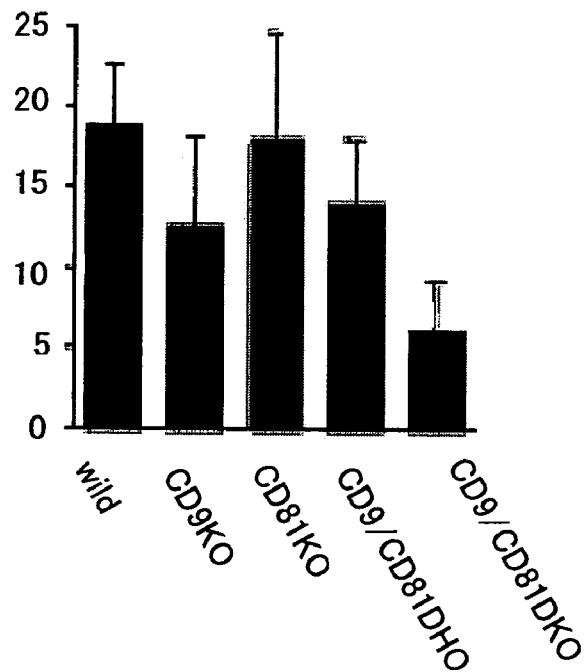
FIG. 11E shows osteoid surface (OS/BS) determined as in FIG. 11A.
Figure 11F:
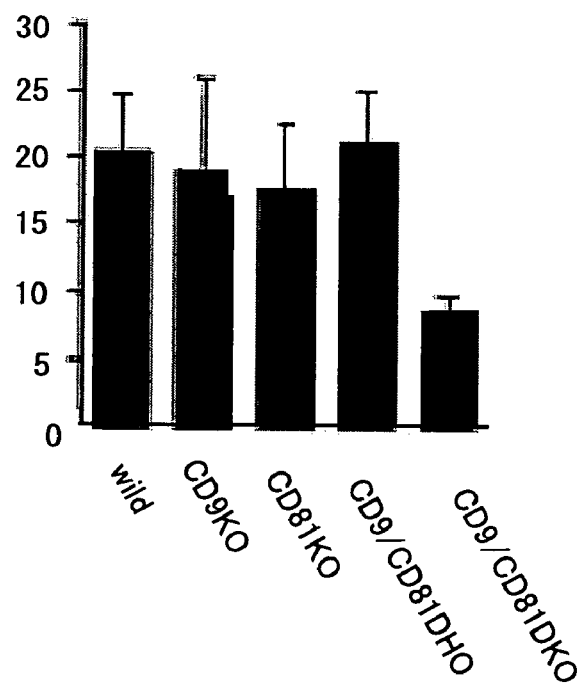
FIG. 11F shows osteoblast surface (Ob.S/BS) determined as in FIG. 11A.

However, osteoid thickness, osteoid surface, and osteoblast surface were significantly decreased in the CD9/CD81 double-deficient mice, suggesting the reduced matrix formation by osteoblasts (FIGS. 11D to 11F).

Figure 11G:
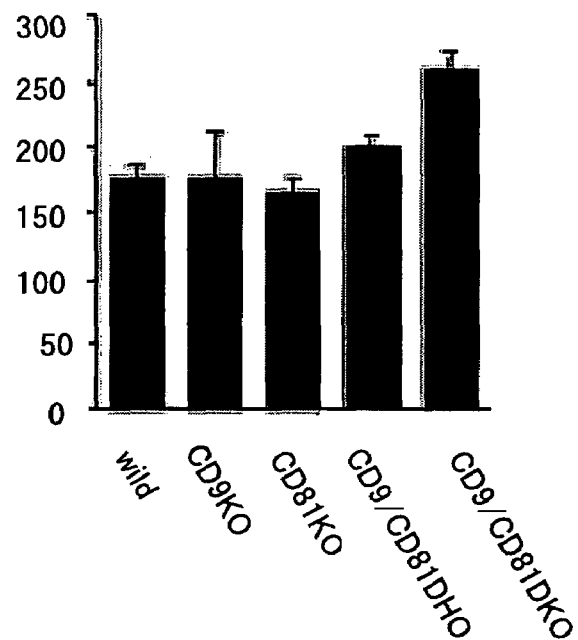
FIG. 11G shows osteoclast number (N.Oc/BPm) determined as in FIG. 11A.
Figure 11H:
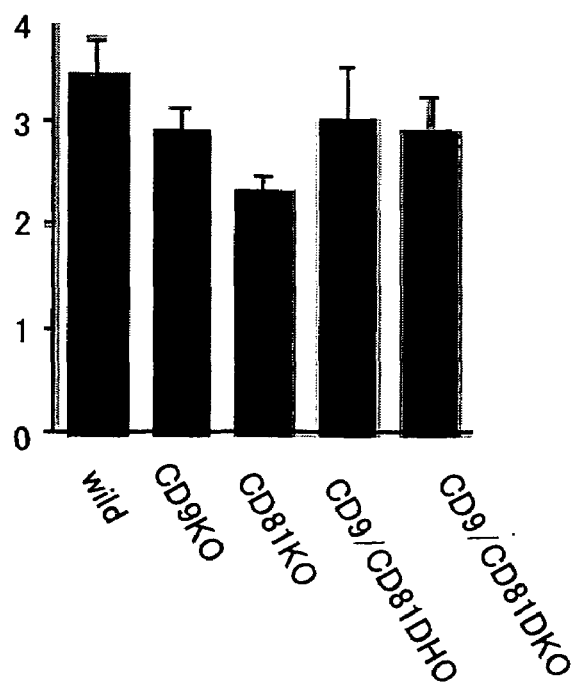
FIG. 11H shows osteoclast surface (Oc.S/BS) determined as in FIG. 11A.

Although the increase in the number of osteoclasts was observed, the osteoclast surface did not increase, suggesting the possibility that osteoclast function was rather reduced (lower panel of FIG. 9, FIGS. 11G and 11H).

Example 6

Next, the function of osteoblast in bone formation and calcification was examined by intraperitoneal injection of calcein in 8-week-old mice.

Calcein assay is an established and commonly used technique to measure bone formation by osteoblasts based on the fact that calcein is taken up into the bone in the process of osteogenesis.

Figure 12B:
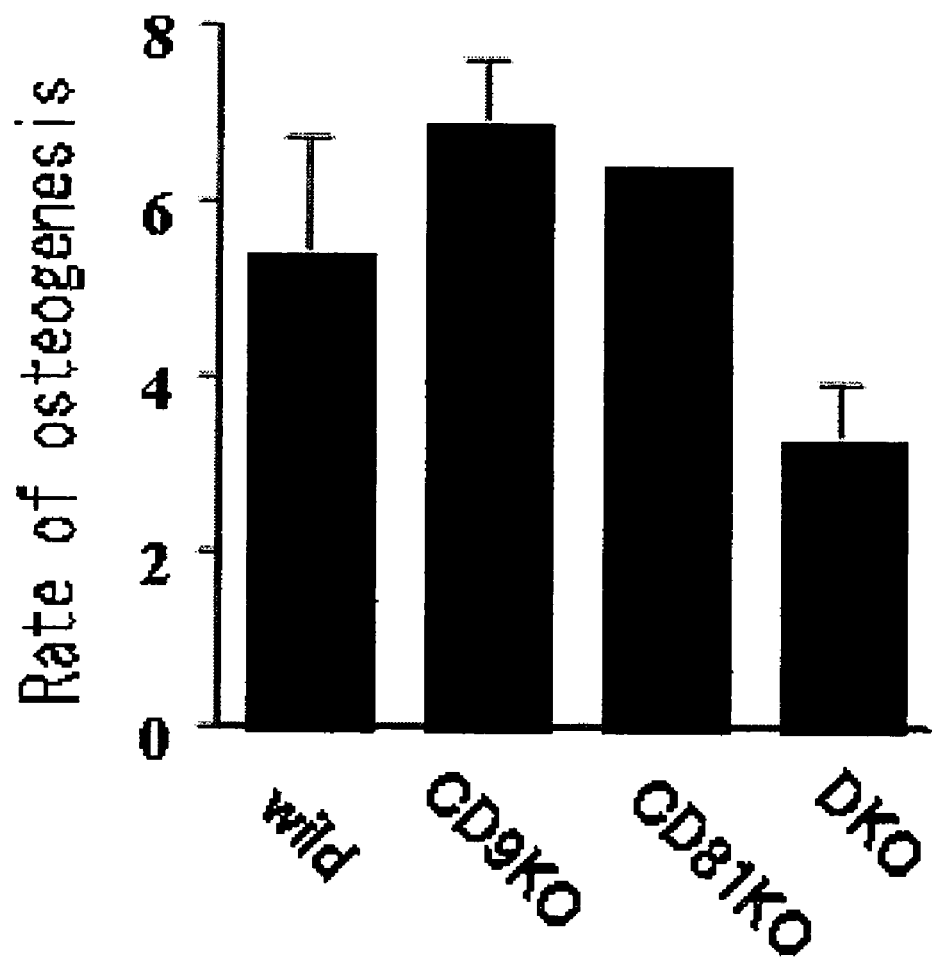
FIG. 12B shows bone formation rate (BFR/BS) determined in the calcein labeling on an 8-week-old wild-type (wild) mice, CD9 deficient (CD9 KO) mice, CD81 deficient (CD81KO) mice, and CD9/CD81 double-deficient (DKO) mice.

Calcein was injected intraperitoneally into the mice twice every 4 days. Undecalcified specimens of femurs were prepared. The calcified area was observed with a fluorescence microscope and the bone formation rate was determined by Osteoplan II (Zeiss) semi-automation system, as shown in FIGS. 12A and 12B.

In the CD9/CD81 double-deficient (DKO) mice, the distance between labeled bands was reduced and the bone formation rate was reduced to about 60% of that of wild-type.

CD9/CD81 double-deficient mice lack membrane proteins CD9 and CD81 and exhibit a pathological condition similar to low-turnover type of osteoporosis, which is frequently observed in aging. Thus, the CD9/CD81 double-deficient mouse could be an animal model of low-turnover type of osteoporosis.

Example 7

Generation of CD9/CD81 Double-Deficient Mice Having CD9 Gene to be Expressed Only in Germ Cells ZP3, which is a gene to be expressed specifically in ovum, was isolated. An EcoRV site was artificially inserted downstream of an about 6 kb fragment containing the promoter of this gene. A vector was prepared by inserting a blunt-ended CD9 structural gene at this EcoRV site, and was used to generate transgenic mice having this gene (TGPzp3::CD9).

Next, the TGPzp3::CD9 was mated with CD9-deficient mice to generate mice, which do not have CD9 gene but have a Pzp3::CD9 gene. The obtained mice expressing CD9 in ovums was able to generate offspring by mating between homozygous females and males.

The thus-obtained CD9 deficient mice having the Pzp3::CD9 gene was mated with CD81 deficient mice obtained in the ordinary way, and thereby, CD9/CD81 double-deficient mice in which both germ cells and somatic cells have a newly introduced CD9 (TGPzp3::CD9), but which mice do not express CD9 in a normal condition was generated.

Example 8

Morphological Analysis of Mouse Lung

Lungs of mice were fixed with 10% formalin under the pressure of 25 cm of water, embedded in a paraffin, and then sections of 5 μm thickness were stained with hematoxylin-eosin. Alveolar space size was measured according to Ray et al. (J Clin Invest 10:2501-2511, 1997). Briefly, a minimum of 10 fields from each mouse lung was randomly acquired. Air space size was quantified by calculating the mean chord length using the NIH Image software. At least 200 measurements per field were made and at least 3 animals were studied for wild-type (Wild) mice and CD9/CD81 double-deficient mice (DKO). For the observation of elastic fibers and mucus-secreting cells, staining with orcein and periodic acid-Schiff (PAS) staining was carried out, respectively.

Figure 13:
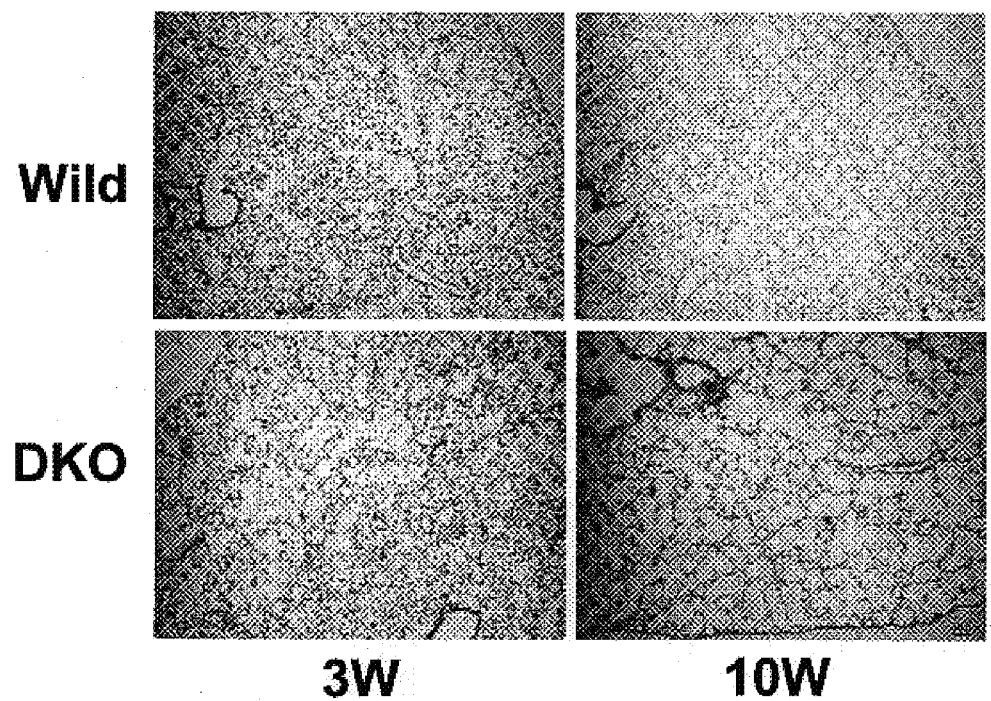
FIG. 13 shows, in Example 8, air space of a wild-type (Wild) mouse and CD9/CD81 double-deficient (DKO) mouse at the age of 3 and 10 weeks. Enlargement of air spaces and infiltration of inflammatory cells in the alveolar walls is observed in the DKO mouse when compared with the wild-type mouse.

In hematoxylin-eosin staining, no significant difference was observed between the lung of the CD9/CD81 double-deficient mice (DKO) and wild-type (Wild) at 3 weeks of age (3 W); however, at 10 weeks of age (10 W), emphysematous change including enlargement of the alveolar space (destruction of alveolar architecture) and infiltration of inflammatory cells mainly comprising mononuclear cells was observed in the CD9/CD81 double-deficient mice (DKO) (FIG. 13). These emphysematous changes were observed little, if any, in the CD9 knockout mice and CD81 knockout mouse at the same age (data not shown).

Figure 14:
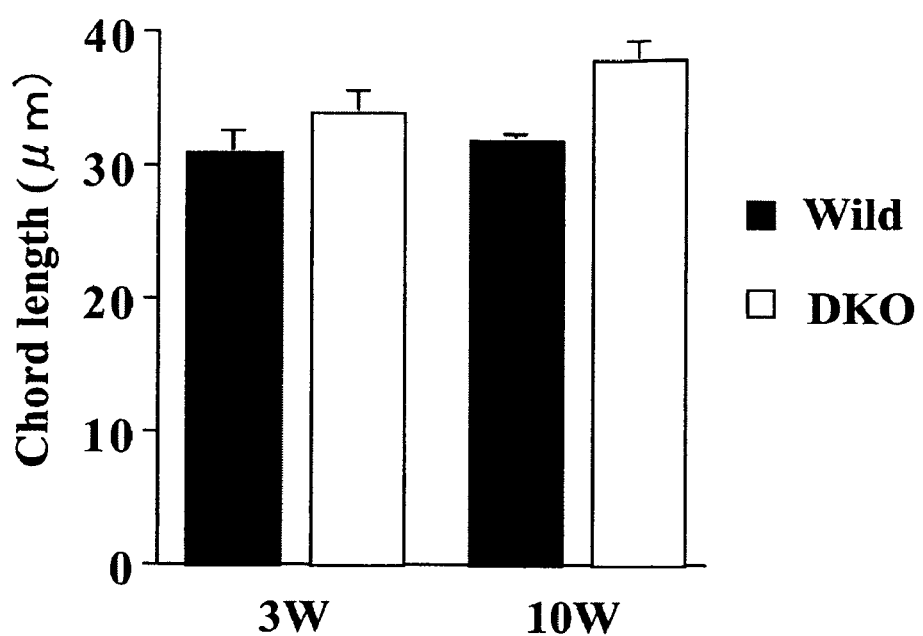
FIG. 14 shows, in Example 8, chord length of a wild-type (Wild) mouse and CD9/CD81 double-deficient (DKO) mouse by morphometry.

Age-dependent enlargement of the alveolar space was confirmed when chord length (alveolar space size) was calculated from tissue specimens using an image program (FIG. 14).

Figure 15:
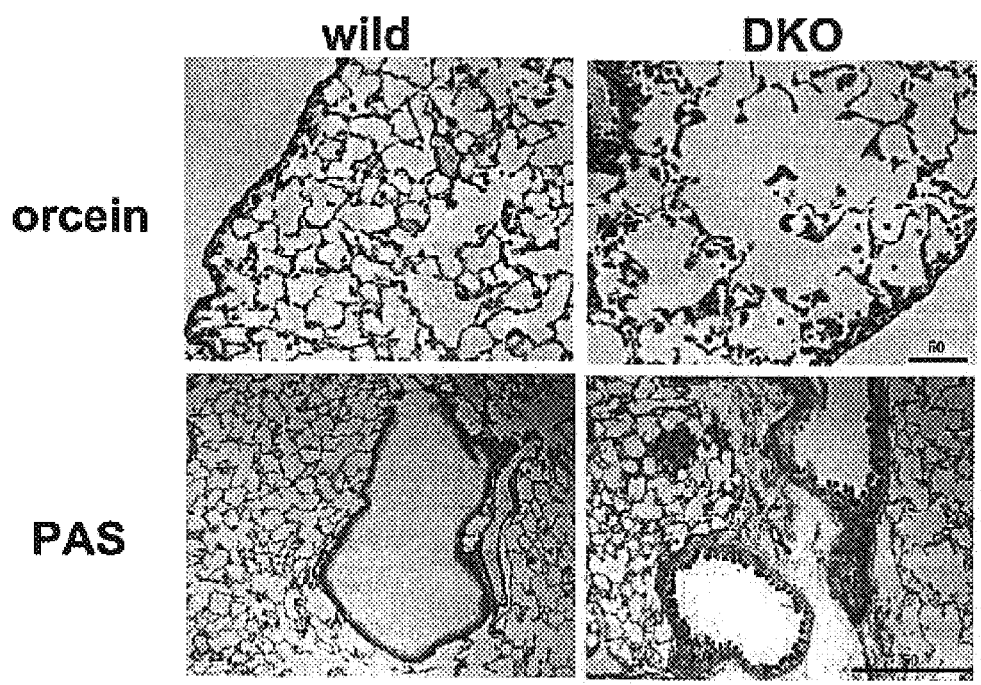
FIG. 15 shows, in Example 8, orcein and periodic acid-Schiff (PAS) staining of a wild-type (Wild) mouse and CD9/CD81 double-deficient mouse (DKO). The destruction of elastic fibers and hyperplasia of secretory cells are observed in DKO mouse.

Furthermore, disruption of elastic fiber and hyperplasia of mucus-secreting cells (stained in red) were observed by orcein stainig and PAS staining, respectively. These histological changes were similar to those seen in COPD (FIG. 15).

Thus, the lung of CD9/CD81 double-deficient mice (DKO) exhibits a pathological condition similar to human COPD.

Example 9

Measurement of MMP Activity

Bronchoalveolar lavage fluids were collected and MMP activity was examined by gelatin zymogram from randomly selected 10-week-old CD9/CD81 double-deficient mice and wild-type mice.

Bronchoalveolar Lavage

Figure 17:
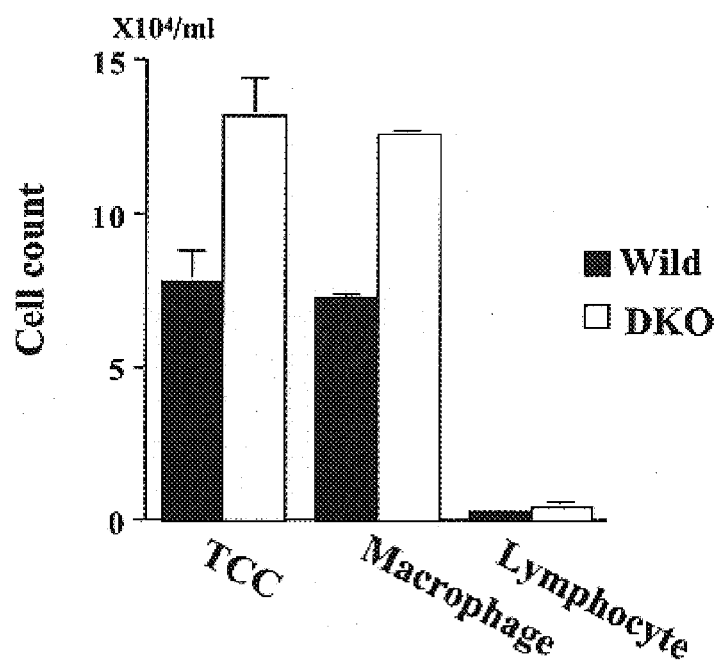
FIG. 17 shows, in Example 9, cell count in the bronchoalveolar lavage fluid of wild-type (Wild) mice and CD9/CD81 double-deficient (DKO) mice. The number of total cells and macrophages are increased in the DKO mice.

Lungs of mice were washed three times with 1 ml of PBS containing 0.1% BSA. Collected cells in the lavage fluid were centrifuged onto Cytospin slides and visualized with Wright stain. The number of total cells, macrophage, and lymphocyte was then calculated. At least 3 mice were analyzed for both the wild-type and CD9/CD81 double-deficient mice (FIG. 17).

Gelatin Zymogram

Four 10-week-old mice were randomly selected from wild-type and CD9/CD81 double-deficient mice, and supernatants of bronchoalveolar lavage fluid were collected and concentrated 10-fold using Centricon 10. The samples were electrophoresed under non-reduced condition in a 10% Zymogram gelatin gels. After Coomassie blue staining and destaining, gelatinolytic activity of MMPs was detected.

Figure 16:
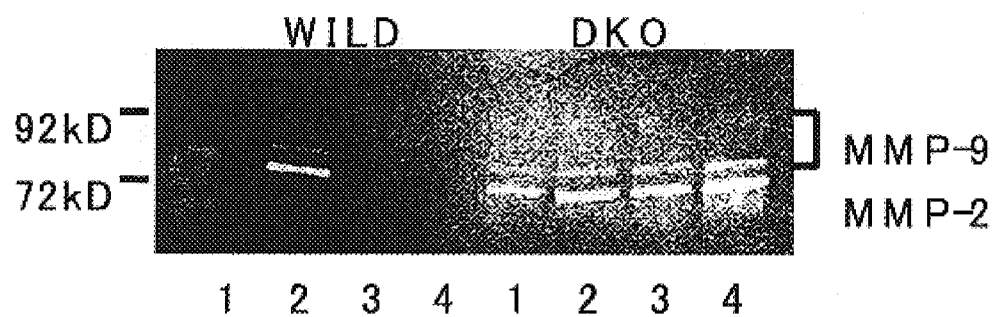
FIG. 16 shows, in Example 9, MMP activity in the bronchoalveolar lavage fluid of wild-type (Wild) mice and CD9/CD81 double-deficient (DKO) mice. MMP-2 and MMP-9 activities are increased in the DKO mice.

When compared with wild-type (Wild), CD9/CD81 double-deficient mice (DKO) showed increased MMP-2 and MMP-9 activities (FIG. 16). Furthermore, the CD9/CD81 double-deficient mice contained the increased number of total cells (TCC), most of which were macrophage, in the BALF (FIG. 17). These results suggest that macrophages were increased and MMP activities were elevated in the lung of CD9/CD81 double-deficient mice. This reflects the elevation of MMP-2 and MMP-9 activities and/or increase of macrophage in human COPD, and indicates that in the CD9/CD81 double-deficient mice, the MMP-2 and MMP-9 activities and/or increase of macrophage in the lung could be one of indexes with relevance to COPD.

In above-mentioned Examples, lung emphysema and hyperplasia of mucus-producing cells were observed in the CD9/CD81 double-deficient mice; thus, the CD9/CD81 double-deficient mouse has lung disease similar to human COPD. Furthermore, the CD9/CD81 double-deficient mouse also shows osteoporosis, which is frequently present in the COPD patients; therefore, the mouse of the present invention is considered to be a disease model reflecting human COPD more accurately than the previously reported genetically-engineered mice, and is useful for the screening of therapeutic agents not only as an osteoporosis model, but also as a COPD model animal.

ADVANTAGEOUS EFFECT OF THE INVENTION

The invention can provide a CD9/CD81 double-deficient non-human animal which accurately represents the pathological conditions of osteoporosis and COPD and can be utilized as a model animal; and a method to use the non-human animal as either an osteoporosis model animal or a COPD model animal.

What is claimed is:

1. A homozygous CD9/CD81 double-deficient mouse, wherein an endogenous gene coding for CD9 and an endogenous gene coding for CD81 are homozygously mutated so that endogenous CD9 protein and CD81 protein are not expressed in the mouse, and
wherein the CD9/CD81 double-deficient mouse displays at least one of a phenotype in which osteogenesis is inhibited and a phenotype similar to chronic obstructive pulmonary disease.

2. The CD9/CD81 double-deficient mouse according to claim 1, wherein the gene coding for CD9 is one of the following (a) and (b), and the gene coding for CD81 is one of the following (c) and (d):
(a) a DNA containing the base sequence of SEQ ID NO: 1,
(b) a DNA which hybridizes under a stringent condition with a DNA complimentary to the DNA containing the base sequence of SEQ ID NO: 1,
(c) a DNA containing the base sequence of SEQ ID NO: 2, and
(d) a DNA which hybridizes under a stringent condition with a DNA complimentary to the DNA containing the base sequence of SEQ ID NO: 2.

3. The CD9/CD81 double-deficient mouse according to claim 1, wherein at least one of a gene coding for CD9 and a gene coding for CD81 is introduced downstream of a promoter of a gene which is expressed specifically in the female germ cells of the mouse, and at least one of the functions of the gene coding for CD9 and the gene coding for CD81 is not deficient in the female germ cells.

4. The CD9/CD81 double-deficient mouse according to claim 1, which is at least one of an osteoporosis model mouse and a chronic obstructive pulmonary disease model mouse.

5. An osteoporosis model mouse method, comprising the steps of:
measuring the degree of osteogenesis of a model mouse that is the CD9/CD81 double-deficient mouse of claim 1;
measuring the degree of osteogenesis in a wild-type mouse; and
comparing the model mouse to the wild-type mouse to assess the degree of inhibition of osteogenesis in the model mouse relative to the wild-type mouse.

6. A method to screen a therapeutic agent for osteoporosis comprising the steps of:
administering a test substance to the CD9/CD81 double-deficient mouse of claim 1; and
evaluating whether or not the test substance has an effect to reduce the inhibition of osteogenesis.

7. A chronic obstructive pulmonary disease mouse model method comprising the steps of:
measuring the degree of a phenotype similar to chronic obstructive pulmonary disease in a model mouse that is the CD9/CD81 double-deficient mouse of claim 1;
measuring the degree of a phenotype similar to chronic obstructive pulmonary disease in a wild-type mouse; and
comparing the degree of the phenotype in the model mouse and in the wild-type mouse.

8. A method to screen a therapeutic agent for chronic obstructive pulmonary disease comprising the steps of:
administering a test substance to the CD9/CD81 double-deficient mouse of claim 1; and
evaluating whether or not the test substance has an effect to reduce the phenotypic similarity to chronic obstructive pulmonary disease.

9. A heterozygous CD9/CD81 double-deficient mouse for use in breeding the homozygous CD9/CD81 double-deficient mouse of claim 1, wherein said heterozygous mouse is heterozygously mutated in an endogenous gene coding for CD9 and an endogenous gene coding for CD81, and wherein breeding of male and female heterozygous CD9/CD81 double deficient mice produces offspring which include the CD9/CD81 double deficient mouse of claim 1.

* * * * *

SEQUENCE LISTING

<160> NUMBER OF SEQ ID NOS: 11

<210> SEQ ID NO 1
<211> LENGTH: 1130

<212> TYPE: DNA
<213> ORGANISM: Mus musculus

<400> SEQUENCE: 1

| | | | | | |
|---|---|---|---|---|---|
| cccttctgtc | ccagtcgttc | gtgcctcttg | tcccacgcaa | ctccagcttg | taccatgccg | 60 |
| gtcaaaggag | gtagcaagtg | catcaaatac | ctgctcttcg | gatttaactt | catcttctgg | 120 |
| ctcgctggca | ttgcagtgct | tgctattgga | ctatggctcc | gattcgactc | tcagaccaag | 180 |
| agcatcttcg | agcaagagaa | taaccattcc | agtttctaca | caggagtgta | cattctgatt | 240 |
| ggagccgggg | ccctcatgat | gctggttggt | ttcctgggct | gctgtggagc | tgtacaagag | 300 |
| tcccagtgca | tgctgggatt | gttcttcggg | ttcctcttgg | tgatattcgc | cattgagata | 360 |
| gccgccgccg | tctggggcta | tacccacaag | gatgaggtga | ttaaagaact | ccaggagttt | 420 |
| tacaaggaca | cctaccaaaa | gttacggagc | aaggatgaac | cccagcggga | aacactcaaa | 480 |
| gccatccata | tggcgttgga | ctgctgtggc | atagctggtc | ctttggagca | gtttatctcg | 540 |
| gacacctgcc | ccaagaaaca | gcttttggaa | agtttccagg | ttaagccctg | ccctgaagcc | 600 |
| atcagtgagg | tcttcaacaa | caagttccac | atcattggag | cagtgggtat | cggcatcgcc | 660 |
| gtggtgatga | tcttcggcat | gatcttcagc | atgatcctgt | gctgcgccat | ccgcaggagc | 720 |
| cgagaaatgg | tctagagtct | gcccaacccc | gagcaggaac | aacggccctg | aagactgtcc | 780 |
| gggccatttg | gtttttttt | gccactaata | ttagtattca | ttatgcattt | ctaaataaca | 840 |
| gtcattctgt | ttgtcctttt | aatgctttat | tcattattga | catttgtagt | tgagggatcc | 900 |
| gggggttcaa | tttattttga | tttttttttt | tggttgttta | ttttgcttg | ttatgttaag | 960 |
| caaaaatcct | gcaatgaaag | gtactatatt | tgccagactc | tagacataag | atattgtaca | 1020 |
| taaagagaat | ttttttgcc | tttaaataga | taaaagtatc | tatcagataa | aaatcaggtt | 1080 |
| gtaagttata | ttgaagacaa | tttgatacat | aataaaagat | tataacagtg | | 1130 |

<210> SEQ ID NO 2
<211> LENGTH: 1510
<212> TYPE: DNA
<213> ORGANISM: Mus musculus

<400> SEQUENCE: 2

| | | | | | |
|---|---|---|---|---|---|
| gcgagcgcgt | ccttgcttca | aagagatagt | gactctcgcg | cctccggcta | ggcctccagc | 60 |
| ccttctctac | cctacgtctc | attctccgca | acgcagttct | ccggcccgca | agcgctccag | 120 |
| gctatctgcc | agtcccggac | cccggtactg | cgtccccata | ccgcccgctc | caggaccaat | 180 |
| ccaagctccg | caggccgcgc | accgccatgg | gggtggaggg | ctgcaccaaa | tgcatcaaat | 240 |
| acctgctctt | cgtcttcaat | ttcgtcttct | ggctggctgg | aggcgtgatc | ctaggtgtag | 300 |
| ctctgtggtt | gcgtcatgat | ccacagacca | ccagcctgct | gtacctggaa | ctgggaaaca | 360 |
| aaccggcacc | caacaccttc | tacgtgggca | tctacattct | cattgctgtg | ggagctgtga | 420 |
| tgatgtttgt | aggcttcctg | gggtgctatg | gggccatcca | ggagtcccag | tgtctgctgg | 480 |
| ggacgttctt | cacctgcctt | gtgatcctgt | ttgcctgtga | ggtggctgca | ggcatctggg | 540 |
| gcttcgtaaa | caaagaccag | atcgccaagg | atgtgaagca | gttctatgac | caggcccttc | 600 |
| agcaagctgt | gatggatgat | gatgccaaca | atgccaaggc | tgtggtgaag | actttccatg | 660 |
| agacgctcaa | ctgttgtggc | tccaacgcac | tgaccacact | gactaccacc | atactgagga | 720 |
| acagcctgtg | tccctcaggc | ggcaacatac | tcaccccctt | actgcagcaa | gattgtcatc | 780 |
| agaaaatcga | tgagctcttc | tctgggaagc | tgtacctcat | tggaattgca | gccattgtgg | 840 |

```
tagctgtcat tatgatcttt gagatgattc tgagcatggt gctgtgctgt ggcatccgga      900
acagctccgt gtactgaggc cctttgcatt gcaccagagg atccctggag tgaccagagg      960
ccaccttggg ggacatggcc tgtgtatata atatttctgt atcactctgc tacacttagt     1020 cttttactt ttgagttttt tgttttgttt tgttttgttt ttgttttagt ttttttttg      1080 tcctgaactt ttcctgttac cttttgggag ctgacatcac acatgggtgg catatgtggg     1140
atgtaggggt ggagctggcc ctggcttgca gggccctgta cgtctgggac ccctggagag     1200
ttctgcctgc tgagccaaac ctcctctaca gctacttgcc cagaggcttt gtagcctagc     1260
tagagggcca tgcccaccca ctcaacccac tgtgggtcac attgctcaca tctttttaat     1320
ctttgttcct ttcctgcctc catttcaaga gctgggtttg taagccctct tatgccttca     1380
atgcacttat tctttctaac gtgtcacctt caactgtaat taaatcttga aacagtcatt     1440
taataaagga ggaaaaaaat caggcaaaaa aaaaaaaaaa aaaaaaaaaa aaaaaaaaaa     1500
aaaaaaaaaa                                                             1510

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:  a primer
      for the detection of the CD9 recombination site

<400> SEQUENCE: 3
aatgggctga ccgcttcctc g                                                  21

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence:Description
      of Artificial Sequence:  a primer for the detection of the CD9
      recombination site

<400> SEQUENCE: 4
cctccctcag gagtgtacat tc                                                 22

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:Description
      of Artificial Sequence:  a primer for the detection of the CD9
      recombination site

<400> SEQUENCE: 5
gaggaacccg aagaactaga agac                                               24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence:Description
      of Artificial Sequence:  a primer for the detection of the CD81
      recombination site

<400> SEQUENCE: 6
tgtgaggtgg ctgcaggcat ctgg                                               24
```

-continued

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence:Description
      of Artificial Sequence: a primer for the detection of the CD81
      recombination site

<400> SEQUENCE: 7
tctcatggaa agtcttcacc acag                                          24

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence:Description
      of Artificial Sequence: a primer for the detection of the CD81
      recombination site

<400> SEQUENCE: 8
gtatccatca tggctgatgc aa                                            22

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:Description
      of Artificial Sequence: a primer for the detection of the CD81
      recombination site

<400> SEQUENCE: 9
agctccaccc ctacatccca c                                             21

<210> SEQ ID NO 10
<211> LENGTH: 226
<212> TYPE: PRT
<213> ORGANISM: Mus musculus

<400> SEQUENCE: 10

Met Pro Val Lys Gly Gly Ser Lys Cys Ile Lys Tyr Leu Leu Phe Gly
1               5                   10                  15

Phe Asn Phe Ile Phe Trp Leu Ala Gly Ile Ala Val Leu Ala Ile Gly
            20                  25                  30

Leu Trp Leu Arg Phe Asp Ser Gln Thr Lys Ser Ile Phe Glu Gln Glu
        35                  40                  45

Asn Asn His Ser Ser Phe Tyr Thr Gly Val Tyr Ile Leu Ile Gly Ala
    50                  55                  60

Gly Ala Leu Met Met Leu Val Gly Phe Leu Gly Cys Cys Gly Ala Val
65                  70                  75                  80

Gln Glu Ser Gln Cys Met Leu Gly Leu Phe Phe Gly Phe Leu Leu Val
                85                  90                  95

Ile Phe Ala Ile Glu Ile Ala Ala Ala Val Trp Gly Tyr Thr His Lys
            100                 105                 110

Asp Glu Val Ile Lys Glu Leu Gln Glu Phe Tyr Lys Asp Thr Tyr Gln
        115                 120                 125

Lys Leu Arg Ser Lys Asp Glu Pro Gln Arg Glu Thr Leu Lys Ala Ile
    130                 135                 140

-continued

His Met Ala Leu Asp Cys Cys Gly Ile Ala Gly Pro Leu Glu Gln Phe
145                 150                 155                 160

Ile Ser Asp Thr Cys Pro Lys Lys Gln Leu Leu Glu Ser Phe Gln Val
                165                 170                 175

Lys Pro Cys Pro Glu Ala Ile Ser Glu Val Phe Asn Asn Lys Phe His
            180                 185                 190

Ile Ile Gly Ala Val Gly Ile Gly Ile Ala Val Val Met Ile Phe Gly
        195                 200                 205

Met Ile Phe Ser Met Ile Leu Cys Cys Ala Ile Arg Arg Ser Arg Glu
    210                 215                 220

Met Val
225

<210> SEQ ID NO 11
<211> LENGTH: 236
<212> TYPE: PRT
<213> ORGANISM: Mus musculus

<400> SEQUENCE: 11

Met Gly Val Glu Gly Cys Thr Lys Cys Ile Lys Tyr Leu Leu Phe Val
1               5                   10                  15

Phe Asn Phe Val Phe Trp Leu Ala Gly Gly Val Ile Leu Gly Val Ala
                20                  25                  30

Leu Trp Leu Arg His Asp Pro Gln Thr Thr Ser Leu Leu Tyr Leu Glu
            35                  40                  45

Leu Gly Asn Lys Pro Ala Pro Asn Thr Phe Tyr Val Gly Ile Tyr Ile
        50                  55                  60

Leu Ile Ala Val Gly Ala Val Met Met Phe Val Gly Phe Leu Gly Cys
65                  70                  75                  80

Tyr Gly Ala Ile Gln Glu Ser Gln Cys Leu Leu Gly Thr Phe Phe Thr
                85                  90                  95

Cys Leu Val Ile Leu Phe Ala Cys Glu Val Ala Ala Gly Ile Trp Gly
                100                 105                 110

Phe Val Asn Lys Asp Gln Ile Ala Lys Asp Val Lys Gln Phe Tyr Asp
            115                 120                 125

Gln Ala Leu Gln Gln Ala Val Met Asp Asp Asp Ala Asn Asn Ala Lys
        130                 135                 140

Ala Val Val Lys Thr Phe His Glu Thr Leu Asn Cys Cys Gly Ser Asn
145                 150                 155                 160

Ala Leu Thr Thr Leu Thr Thr Thr Ile Leu Arg Asn Ser Leu Cys Pro
                165                 170                 175

Ser Gly Gly Asn Ile Leu Thr Pro Leu Leu Gln Gln Asp Cys His Gln
            180                 185                 190

Lys Ile Asp Glu Leu Phe Ser Gly Lys Leu Tyr Leu Ile Gly Ile Ala
        195                 200                 205

Ala Ile Val Val Ala Val Ile Met Ile Phe Glu Met Ile Leu Ser Met
    210                 215                 220

Val Leu Cys Cys Gly Ile Arg Asn Ser Ser Val Tyr
225                 230                 235